(12) United States Patent
Sukumaran et al.

(10) Patent No.: US 11,800,995 B2
(45) Date of Patent: *Oct. 31, 2023

(54) PATIENT SUPPORT APPARATUS WITH AUTOMATIC EXIT DETECTION MODES OF OPERATION

(71) Applicant: Stryker Corporation, Kalamazoo, MI (US)

(72) Inventors: Sujay Sukumaran, Portage, MI (US); Celso Henrique Farnese Pires Pereira, Portage, MI (US); Grady Sertic, St. Louis, MO (US); Placide Nibakuze, Kalamazoo, MI (US); Anish Paul, Portage, MI (US); Krishna Sandeep Bhimavarapu, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/982,135

(22) Filed: Nov. 7, 2022

(65) Prior Publication Data

US 2023/0067526 A1    Mar. 2, 2023

Related U.S. Application Data

(63) Continuation of application No. 17/318,476, filed on May 12, 2021, now Pat. No. 11,490,834.
(Continued)

(51) Int. Cl.
*A61B 5/11* (2006.01)
*A61B 5/00* (2006.01)
(Continued)

(52) U.S. Cl.
CPC .......... *A61B 5/1115* (2013.01); *A61B 5/6892* (2013.01); *A61B 5/746* (2013.01);
(Continued)

(58) Field of Classification Search
CPC ..... A61B 5/1115; A61B 5/6892; A61B 5/746; A61B 2562/0252; A61B 2562/046;
(Continued)

(56) References Cited

U.S. PATENT DOCUMENTS

| 5,276,432 A * | 1/1994 | Travis | G08B 21/22 |
| | | | 177/144 |
| 7,253,366 B2 * | 8/2007 | Bhai | G16H 40/63 |
| | | | 177/144 |

(Continued)

*Primary Examiner* — Zhen Y Wu
(74) *Attorney, Agent, or Firm* — Warner Norcross + Judd LLP

(57) ABSTRACT

A patient support apparatus, such as a bed, cot, stretcher, etc., for supporting a patient includes an exit detection system with multiple user-selectable modes of operation that each have different sensitivity levels for triggering an exit alert. The exit detection system also includes one or more non-user selectable modes of operation that are automatically implemented in response to a triggering action. For example, a transition mode may be automatically implemented when the user attempts to switch from a first user-selectable mode to a different user selectable mode, or a motion mode may be automatically implemented when movement of one or more components of the patient support apparatus occurs. In the transition mode, the exit detection system may use a least restrictive sensitivity level. In the motion mode, the exit detection system may inhibit exit alerts and/or change the criteria for issuing the exit alert.

20 Claims, 9 Drawing Sheets

Related U.S. Application Data

(60) Provisional application No. 63/024,066, filed on May 13, 2020.

(51) Int. Cl.
*A61G 7/05* (2006.01)
*G08B 21/04* (2006.01)
*G08B 21/18* (2006.01)

(52) U.S. Cl.
CPC ........ *A61G 7/0528* (2016.11); *G08B 21/0461* (2013.01); *G08B 21/182* (2013.01); *A61B 2562/0252* (2013.01); *A61B 2562/046* (2013.01); *A61G 7/0507* (2013.01); *A61G 2203/20* (2013.01); *A61G 2203/32* (2013.01)

(58) Field of Classification Search
CPC .. G08B 21/046; G08B 21/182; A61G 7/0528; A61G 7/0507; A61G 2203/20; A61G 2203/32
USPC ...................................................... 340/573.4
See application file for complete search history.

(56) References Cited

U.S. PATENT DOCUMENTS

| | | | | |
|---|---|---|---|---|
| 10,292,605 | B2* | 5/2019 | Vanderpohl, III | A61B 5/1102 |
| 2006/0028350 | A1* | 2/2006 | Bhai | A61B 5/1115 |
| | | | | 177/144 |
| 2007/0157385 | A1* | 7/2007 | Lemire | A61M 5/1415 |
| | | | | 5/618 |
| 2008/0028533 | A1* | 2/2008 | Stacy | A61G 7/015 |
| | | | | 5/713 |
| 2008/0169931 | A1* | 7/2008 | Gentry | A61B 5/1117 |
| | | | | 600/300 |
| 2011/0068928 | A1* | 3/2011 | Riley | A61B 5/6887 |
| | | | | 340/573.1 |
| 2011/0112442 | A1* | 5/2011 | Meger | A61B 5/4818 |
| | | | | 600/595 |
| 2012/0259245 | A1* | 10/2012 | Receveur | A61G 7/0524 |
| | | | | 5/616 |
| 2012/0259248 | A1* | 10/2012 | Receveur | A61G 7/0514 |
| | | | | 600/595 |
| 2014/0124273 | A1* | 5/2014 | Receveur | G01G 19/445 |
| | | | | 177/7 |
| 2016/0078740 | A1* | 3/2016 | Pirio | A61G 7/0527 |
| | | | | 340/573.4 |
| 2016/0106345 | A1* | 4/2016 | Kostic | A61B 5/1116 |
| | | | | 5/652 |
| 2016/0327426 | A1* | 11/2016 | Nachtigal | A61G 7/0527 |
| 2016/0371950 | A1* | 12/2016 | Yasukawa | A61B 5/0077 |
| 2017/0098359 | A1* | 4/2017 | Sidhu | A61G 7/015 |
| 2017/0234723 | A1* | 8/2017 | Charles | A61G 7/015 |
| | | | | 5/600 |
| 2019/0183428 | A1* | 6/2019 | Fu | A61B 5/1115 |
| 2021/0315755 | A1* | 10/2021 | Matsubayashi | A61G 7/018 |

* cited by examiner

User-Selectable Modes

1st Mode
- Alert if C.O.G. outside first zone with first boundary
- Alert if patient weight decreases by 50% or more — 130a

2nd Mode
- Alert if C.O.G. outside second zone with second boundary
- Alert if patient weight decreases by 50% or more — 130b

3rd Mode
- Alert if C.O.G. outside third zone with third boundary
- Alert if patient weight decreases by 50% or more — 130c

Automatic Modes

Transition Mode A — 134a
- Alert if C.O.G. outside least restrictive zone with least restrictive boundary
- Alert if patient weight decreases bt 50% or more

Transition Mode B — 134b
- No alert if C.O.G. outside any zone
- Alert if patient weight decreases by 50% or more

Motion Mode A — 136a
- Stop C.O.G. calculations and any C.O.G.-based alerts
- Alert if patient weight decreases by 50% or more
- Adjust zone boundaries after motion stops and return to previous active mode

Motion Mode B — 136b
- Continue C.O.G. calculations but inhibit alert if C.O.G. outside active zone
- Alert if patient weight decreases by 50% or more
- Adjust zone boundaries after motion stops and return to previous active mode

Motion Mode C — 136c
- Continue C.O.G. calculations and adjust boundaries of active zone as component(s) move
- Alert if C.O.G. outside adjusted boundary of active zone
- Alert if patient weight decreases by 50% or more
- Return to previous active mode and use adjusted boundaries when motion stops

FIG. 6

PATIENT SUPPORT APPARATUS WITH AUTOMATIC EXIT DETECTION MODES OF OPERATION

CROSS-REFERENCE TO RELATED APPLICATIONS

This application claims priority to U.S. patent application Ser. No. 17/318,476 filed May 12, 2021, by inventors Sujay Sukumaran et al. and entitled PATIENT SUPPORT APPARATUS WITH AUTOMATIC EXIT DETECTION MODES OF OPERATION, which in turn claims priority to U.S. provisional patent application Ser. No. 63/024,066 filed May 13, 2020, by inventors Grady Sertic et al. and entitled PATIENT SUPPORT APPARATUS WITH AUTOMATIC EXIT DETECTION MODES OF OPERATION, the complete disclosures of both of which are incorporated herein by reference.

BACKGROUND

The present disclosure relates to patient support apparatuses, such as beds, cots, stretchers, operating tables, recliners, or the like. More specifically, the present disclosure relates to patient support apparatuses that include sensors for monitoring the motion and/or activity of an occupant of the patient support apparatus and issuing an alert if the occupant is, or may be, about to exit the patient support apparatus.

Existing hospital beds and/or stretchers often include an exit detection system that is adapted to detect when a patient has exited the bed, or when a patient may be about to exit the bed. Typically, such beds include circuitry for providing an audio or visual alert when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately. The exit detection system itself may be implemented in a variety of manners, including using a plurality of force sensors. In general, it is desirable to implement the exit detection system so as to minimize false alerts, but also prevent the patient from being able to exit the bed without an alert being issued while the exit detection system is armed.

SUMMARY

According to various embodiments, an improved patient support apparatus is provided that helps reduce false alerts and/or helps reduce the ability of a patient to exit without detection by the exit detection system when the exit detection system is armed. In some embodiments, the exit detection system is adapted to automatically change to a transition mode when the user attempts to switch from a first user-selectable mode to a second user-selectable mode. The transition mode is initiated when the user activates a corresponding control and lasts until the exit detection system actually makes the switch or until the exit detection system is unable to make the switch and the user ceases to retry making the switch. In the transition mode, the exit detection system may relax the sensitivity of the exit detection system, but continue to monitor for movement of the patient indicative of exit. In some embodiments, the exit detection system is adapted to automatically change to a motion mode when movement of any of the components of the patient support apparatus is detected. In the motion mode, the exit detection system changes its operation in one or more manners, such as inhibiting some exit alerts that are based on specific criteria, stopping all alerts, and/or recalculating movement thresholds dynamically while the component(s) are in motion so as to account for movement of those component(s). Still other features will be apparent to those skilled in the art in light of the following description and accompanying claims.

According to one embodiment of the present disclosure, a patient support apparatus is provided that includes a frame, a support surface, an exit detection system, and a control panel. The support surface is supported by the frame and is adapted to support a patient thereon. The exit detection system is adapted to be armed and disarmed and to operate, when armed, in a first mode with a first sensitivity level or in a second mode with a second sensitivity level. The exit detection system is further adapted to issue an alert if movement of the patient beyond a first threshold occurs while operating in the first mode and to issue the alert if movement of the patient beyond a second threshold occurs while operating in the second mode. The control panel communicates with the exit detection system and is adapted to allow a user to arm and disarm the exit detection system and to change the exit detection system from the first mode to the second mode. The exit detection system is further adapted to, in response to the user activating a control to change from the first mode to the second mode, to operate in a transition mode during a transition period defined between a first moment when the user activates the control and a second moment when the exit detection system actually begins operating in the second mode or returns to the first mode. The exit detection system is still further adapted to issue the alert if movement of the patient beyond a transition threshold occurs while operating in the transition mode.

According to other aspects of the present disclosure, the transition threshold may correspond to whichever of the first and second sensitivity levels is smaller, thereby giving the patient more latitude to move during the transition period without triggering the alert.

In some embodiments, the exit detection system is further adapted to operate in a third mode with a third sensitivity level different from the first and second sensitivity levels, and the transition threshold corresponds to whichever one of the first, second, and third sensitivity levels has the least sensitivity.

The patient support apparatus, in some embodiments, includes an exit detection system that is comprised of a plurality of force sensors adapted to detect forces exerted by the patient on the support surface and a controller in communication with the plurality of force sensors. The plurality of force sensors are, in some embodiments, load cells.

In some embodiments, the exit detection system is further adapted to perform a transition task during the transition period. The transition task is a prerequisite for changing from the first mode to the second mode, and the control panel includes a display adapted to display a message during the transition period if the exit detection system is unable to complete the transition task. In some such embodiments, the exit detection system is further adapted to present the user with a retry choice or a cancel choice on the display if the exit detection system is unable to complete the transition task. The retry choice comprises re-attempting to change from the first mode to the second mode and the cancel choice comprises canceling the change of the exit detection system from the first mode to the second mode. Still further, in some such embodiments, the exit detection system is further adapted to await a predetermined time period after presenting the user with the retry and cancel choices and, if the user does not make a choice, to automatically stop operating in the transition mode and to return to operating in the first mode.

In some embodiments, the transition task includes any one or more of: (a) taking stable readings from a plurality of force sensors for a predetermined period of time; (b) confirming that a brake on the patient support apparatus is engaged; and/or confirming that the patient support apparatus is not operating on power from a battery having a charge level below a predetermined charge threshold.

The exit detection system, in some embodiments, is further adapted to continue to operate in the transition mode until either the exit detection system changes to operating in the second mode or the user discontinues attempts to change the exit detection system to operating in the second mode. The exit detection system may also be adapted to automatically return to operating in the first mode if the user discontinue attempts to change the exit detection system to the second mode.

In some embodiments, the patient support apparatus further comprises a motion controller in communication with the exit detection system. The motion controller is adapted to control movement of a plurality of the components of the patient support apparatus. In such embodiments, the exit detection system is further adapted to override its current mode of operation with a motion mode of operation when any of the plurality of components are moving, and to cease operating in the motion mode when all movement of the plurality of components stops.

The exit detection system, in some embodiments, is adapted to not issue the alert when operating in the motion mode if movement of the patient beyond any of the first threshold, second threshold, or transition thresholds occurs. The exit detection system may include a plurality of force sensors adapted to detect a weight of the patient and the exit detection system may be adapted to issue the alert in the motion mode only if the weight of the patient decreases by ten percent or more.

The exit detection system may be adapted to calculate a center of gravity of the patient while operating in any of the first, second, or transition modes, and to stop calculating the center of gravity of the patient while operating in the motion mode.

In some embodiments, the exit detection system includes a plurality of force sensors adapted to detect a weight of the patient and the exit detection system is adapted to perform the following while operating in the motion mode: (a) determine whether movement of the patient beyond any of the first, second, or transition thresholds occurs but not issue the alert if movement beyond any of the first, second, or transition thresholds occurs; (b) issue the alert if the weight of the patient decreases by ten percent or more; and (c) when all movement of the plurality of components stops, automatically begin operating in whichever mode the exit detection system was operating in prior to commencement of the motion mode.

The first, second, and transition thresholds, in some embodiments, correspond to first, second, and transition zones, respectively, that each define permitted areas of movement of a center of gravity of the patient. In such embodiments, the exit detection system may be adapted to recalculate a boundary of the first, second, and/or transition zone while operating in the motion mode. Such recalculation varies depending upon which specific one or more of the plurality of components is moving while the exit detection system is in the motion mode.

According to another embodiment of the present disclosure, a patient support apparatus is provided that includes a frame, a support surface, an exit detection system, and a control panel. The support surface is supported by the frame and adapted to support a patient thereon. The exit detection system is adapted to be armed and disarmed, as well as to operate, when in the armed state, in a first mode with a first sensitivity level or in a second mode with a second sensitivity level. The exit detection system is further adapted to issue an alert if movement of the patient beyond a first threshold occurs while operating in the first mode and to issue the alert if movement of the patient beyond a second threshold occurs while operating in the second mode. The control panel communicates with the exit detection system and is adapted to allow a user to arm and disarm the exit detection system and to change the exit detection system from the first mode to the second mode. The exit detection system is further adapted to perform the following, in response to the user activating a control to change from the first mode to the second mode: (a) to attempt to complete a transition task wherein the transition task is a prerequisite to changing from the first mode to the second mode; (b) to notify the user if the exit detection system is unable to complete the transition task; (c) to present the user with a retry choice and a cancel choice, wherein the retry choice comprises re-attempting to change from the first mode to the second mode and the cancel choice comprises canceling changing from the first mode to the second mode; (d) to await a predetermined time period after presenting the user with the retry and cancel choices; and (e) to automatically return to operating in the first mode if the user does not select the retry choice or the cancel choice within the predetermined time period.

According to other aspects of the present disclosure, the exit detection system includes a plurality of force sensors and the transition task includes one or more of the following: (a) taking stable readings from the plurality of force sensors for a predetermined period of time; (b) confirming that a brake on the patient support apparatus is engaged; and (c) confirming that the patient support apparatus is not operating on power from a battery having a charge level below a predetermined charge threshold.

In some embodiments, the exit detection system is further configured to operate in a transition mode during a transition period defined between a first moment when the user activates the control and a second moment when the exit detection system actually begins operating in the second mode or the exit detection system automatically returns to operating in the first mode. In such embodiments, the exit detection system is adapted to issue the alert if movement of the patient beyond a transition threshold occurs while the exit detection system is operating in the transition mode. The transition threshold corresponds to a threshold less restrictive than at least one of the first and second sensitivity levels.

In some embodiments, the exit detection system is further adapted to operate in a third mode with a third sensitivity level different from the first and second sensitivity levels, and the transition threshold corresponds to whichever one of the first, second, and third sensitivity levels has the least sensitivity.

In some embodiments, the patient support apparatus further comprises a motion controller in communication with the exit detection system, wherein the motion controller is adapted to control movement of a plurality of the components of the patient support apparatus, and the exit detection system is further adapted to override its current mode of operation with a motion mode of operation when any of the plurality of components are moving. The exit detection system is further adapted to cease operating in the motion mode when all movement of the plurality of components stops.

In some embodiments, the exit detection system is adapted to not issue the alert when operating in the motion mode if movement of the patient beyond any of the first threshold, second threshold, or transition thresholds occurs.

In some embodiments, the exit detection system includes a plurality of force sensors adapted to detect a weight of the patient and the exit detection system is adapted to issue the alert in the motion mode only if the weight of the patient decreases by ten percent or more.

In some embodiments, the exit detection system is adapted to calculate a center of gravity of the patient while operating in any of the first, second, or transition modes, and the exit detection system is further adapted to stop calculating the center of gravity of the patient while operating in the motion mode.

The exit detection system may include a plurality of force sensors adapted to detect a weight of the patient and it may be adapted to perform the following while operating in the motion mode: (a) determine whether movement of the patient beyond any of the first, second, or transition thresholds occurs but not issue the alert if movement beyond any of the first, second, or transition thresholds occurs; (b) issue the alert if the weight of the patient decreases by ten percent or more; and (c) when all movement of the plurality of components stops, automatically begin operating in whichever mode the exit detection system was operating in prior to commencement of the motion mode.

In some embodiments, the first, second, and transition thresholds correspond to first, second, and transition zones, respectively, that each define permitted areas of movement of a center of gravity of the patient. In such embodiments, the exit detection system may be adapted to recalculate a boundary of the first, second, and/or transition zone while operating in the motion mode, wherein the recalculation varies based upon which specific one or more of the plurality of components is moving while in the motion mode.

A patient support apparatus according to another embodiment of the present disclosure includes a frame, a support surface, an exit detection system, a motion controller, and a control panel. The support surface is supported by the frame and adapted to support a patient thereon. The exit detection system is adapted to be armed and disarmed and to operate, when armed, in a first mode with a first sensitivity level or in a second mode with a second sensitivity level. The exit detection system is further adapted to issue an alert if movement of the patient beyond a first threshold occurs while operating in the first mode and to issue the alert if movement of the patient beyond a second threshold occurs while operating in the second mode. The motion controller is in communication with the exit detection system and is adapted to control movement of a plurality of components of the patient support apparatus. The control panel is in communication with the exit detection system and is adapted to allow a user to arm and disarm the exit detection system and to change the exit detection system from the first mode to the second mode. The exit detection system is also adapted to override its current mode of operation with a motion mode of operation when any of the plurality of components are moving, and to cease operating in the motion mode when all movement of the plurality of components stops, wherein the exit detection system generates the alert while in the motion mode of operation in a manner different from how the exit detection system generates the alert while in either the first mode or second mode of operation.

In some embodiments, the exit detection system further includes a plurality of load cells adapted to detect a weight of the patient, and the exit detection system is further adapted to not issue the alert when operating in the motion mode if movement of the patient beyond either of the first threshold or second threshold occurs, but to issue the alert in the motion mode if the weight of the patient decreases by ten percent or more.

The exit detection system, in some embodiments, is adapted to calculate a center of gravity of the patient while operating in either of the first or second modes, and to stop calculating the center of gravity of the patient while operating in the motion mode.

In some embodiments, the first and second thresholds correspond to first and second zones, respectively, that each define permitted areas of movement of a center of gravity of the patient. In such embodiments, the exit detection system may be adapted to recalculate a boundary of the first or second zone while operating in the motion mode, wherein the recalculation varies based upon which specific one or more of the plurality of components is moving while in the motion mode.

In some embodiments, the exit detection system is further adapted to perform the following, in response to the user activating a control to change from the first mode to the second mode: (a) to attempt to complete a transition task wherein the transition task is a prerequisite to changing from the first mode to the second mode; (b) to notify the user if the exit detection system is unable to complete the transition task; (c) to present the user with a retry choice and a cancel choice, wherein the retry choice comprises re-attempting to change from the first mode to the second mode and the cancel choice comprises canceling changing from the first mode to the second mode; (d) to await a predetermined time period after presenting the user with the retry and cancel choices; and (e) to automatically return to operating in the first mode if the user does not select the retry choice or the cancel choice within the predetermined time period.

The exit detection system may include a plurality of force sensors and the transition task may include all of the following: (a) taking stable readings from the plurality of force sensors for a predetermined period of time; (b) confirming that a brake on the patient support apparatus is engaged; and (c) confirming that the patient support apparatus is not operating on power from a battery having a charge level below a predetermined charge threshold.

In some embodiments, the exit detection system is further configured to operate in a transition mode during a transition period defined between a first moment when the user activates the control and a second moment when the exit detection system actually begins operating in the second mode or the exit detection system automatically returns to operating in the first mode. In such embodiments, the exit detection system is adapted to issue the alert if movement of the patient beyond a transition threshold occurs while the exit detection system is operating in the transition mode.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 6 is a diagram of a plurality of user-selectable and automatically-selected modes of operation of the exit detection system of the patient support apparatus;

DETAILED DESCRIPTION OF THE EMBODIMENTS

Figure 1:
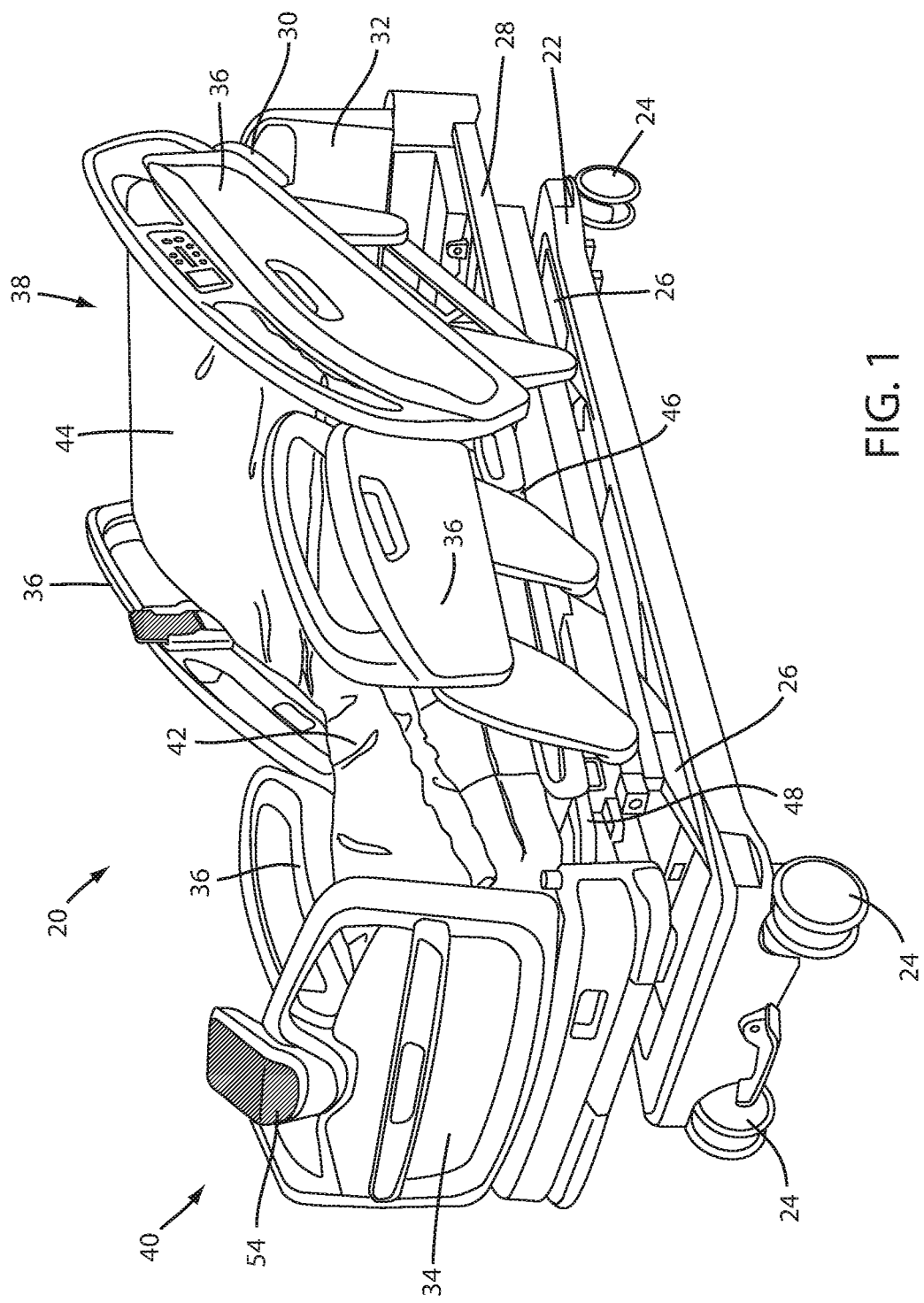
FIG. 1 is a perspective view of a patient support apparatus according to one embodiment of the disclosure.

An illustrative patient support apparatus 20 that may incorporate one or more aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, a residential bed, or any other structure capable of supporting a patient, whether stationary or mobile and/or whether medical or residential.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a headboard 32, a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36. In some embodiments, siderails 36 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width. Notionally, the first standard width may be considered a 36 inch width, the second intermediate width may be considered a 42 inch width and the third more expanded width may be considered a 48 inch width, although these numerical widths may be varied to comprise different width values.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Figure 2:
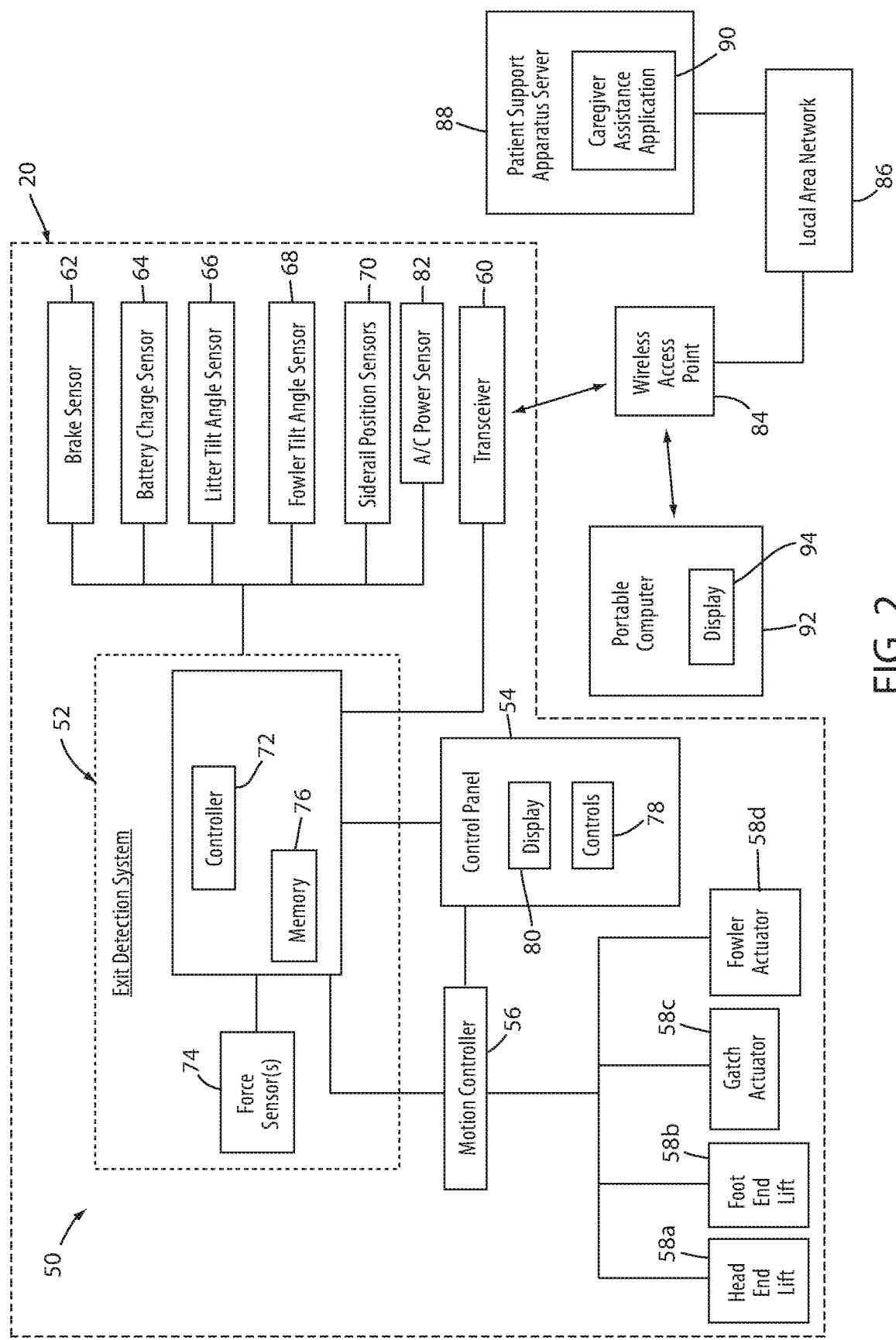
FIG. 2 is a diagram of a control system of the patient support apparatus of FIG. 1, as well as several external devices with which the patient support apparatus may be configured to communicate.

As shown in FIG. 2, patient support apparatus 20 includes a control system 50 that controls various aspects of patient support apparatus 20. Control system 50 includes an exit detection system 52, at least one control panel 54, a motion controller 56, a plurality of motorized actuators 58, an off-board communications transceiver 60, a brake sensor 62, a battery charge sensor 64, a litter tilt angle sensor 66, a Fowler tilt angle sensor 68, an alternating current (A/C) power sensor 82, and a plurality of siderail position sensors 70.

Exit detection system 52 includes a controller 72, a plurality of force sensors 74, and a memory 76. Exit detection system 52 is adapted to determine when an occupant, such as, but not limited to, a patient, of patient support apparatus 20 is likely to exit patient support apparatus 20. More specifically, exit detection system 52 is adapted to determine when an occupant is likely to leave prior to the occupant actually leaving, and to issue an alert and/or notification to appropriate personnel so that proper steps can be taken in response to the occupant's imminent departure in a timely fashion. The particular structural details of exit detection system 52 can vary widely from what is shown in FIG. 2.

Force sensors 74 are adapted to detect downward forces exerted by an occupant of support deck 30. Thus, when an occupant is positioned on support deck 30 and remains substantially still (i.e. not moving in a manner involving accelerations that cause forces to be exerted against support deck 30), force sensors 74 will detect the weight of the occupant (as well as the weight of any components of patient support apparatus 20 that are supported—directly or indirectly—by force sensors 74). In at least one embodiment, force sensors 74 are load cells. However, it will be understood by those skilled in the art, that force sensors 74 may be implemented as other types of sensors, such as, but not limited to, linear variable displacement transducers and/or any one or more capacitive, inductive, and/or resistive transducers that are configured to produce a changing output in response to changes in the force exerted against them.

Exit detection controller 72 is constructed of any electrical component, or group of electrical components, that are capable of carrying out the functions described herein. In many embodiments, controller 72 is a conventional microcontroller, although not all such embodiments need include a microcontroller. In general, controller 72 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. Indeed, in some embodiments, exit detection controller 72 is combined with motion controller 56 and/or with one or more other controllers present on patient support apparatus 20. The instructions followed by controller 72 in carrying out the functions described herein, as well as the data necessary for carrying out these functions, are stored in memory 76, which is accessible to controller 72.

Although patient support apparatus 20 includes a total of four force sensors 74, it will be understood by those skilled in the art that different numbers of force sensors 74 may be used in accordance with the principles of the present disclosure. Force sensors 74, in at least one embodiment, are configured to support litter frame 28. When so configured, force sensors 74 are constructed to provide complete and exclusive mechanical support for litter frame 28 and all of the components that are supported on litter frame 28 (e.g. deck 30, headboard 32, footboard 34, and, in some embodiments, siderails 36). Because of this construction, force sensors 74 are adapted to detect the weight of not only those components of patient support apparatus 20 that are supported by the litter frame 28 (including litter frame 28 itself), but also any objects or persons who are positioned either wholly or partially on support deck 30. By knowing the weight of the components of the patient support apparatus 20 that are supported on litter frame 28, controller 72 is able to determine a tare weight that, when subtracted from a total weight sensed after a patient is supported on support deck 30, yields a patient weight.

In some embodiments, the physical location of the force sensors 74 on patient support apparatus 20 may be modified to be located on the base frame, such as shown in commonly assigned U.S. patent application Ser. No. 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. In other embodiments, the physical location of the force sensors 74 on patient support apparatus 20 may be the same as the position of the load cells disclosed in commonly assigned U.S. patent application Ser. No. 15/266,575 filed Sep. 15, 2016, by inventors Anuj Sidhu et al. and entitled PERSON SUPPORT APPARATUSES WITH EXIT DETECTION SYSTEMS, the complete disclosure of which is also incorporated herein by reference. In still other embodiments, the physical location of the force sensors 74 may be the same as the position of the load cells disclosed in U.S. Pat. No. 7,962,981 issued to Lemire et al. and entitled HOSPITAL BED, the complete disclosure of which is also incorporated herein by reference. In still other embodiments, force sensors 74 may be positioned on patient support apparatus 20 at still other locations.

Motion controller 56 (FIG. 2) is adapted to control the movement of a plurality of components of patient support apparatus 20. These components includes, but are not limited to, a head end lift actuator 58a, a foot end lift actuator 58*b*, a gatch actuator 58*c*, and a Fowler actuator 58*d*. Each of these actuators 58*a-d* may comprise a linear actuator with a motor built therein. In some embodiments, the linear actuator may be of the type disclosed in commonly assigned U.S. patent application Ser. No. 15/449,277 filed Mar. 3, 2017, by inventors Anish Paul et al. and entitled PATIENT SUPPORT APPARATUS WITH ACTUATOR FEEDBACK, the complete disclosure of which is incorporated herein by reference. In other embodiments, other types of powered actuators may be used, such as, but not limited to, hydraulic and/or pneumatic actuators.

In some embodiments, motion controller 56 is a conventional microcontroller that controls the operation of the motors contained with each of actuators 58*a-d*. It will be understood that motion controller 56 may be constructed of any electrical component, or group of electrical components, that are capable of carrying out the functions described herein. In general, controller 56 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. Indeed, in some embodiments, as noted above, motion controller 56 may be combined together with exit detection controller 72 and/or with one or more other controllers present on patient support apparatus 20. The instructions followed by controller 56 in carrying out the functions described herein, as well as the data necessary for carrying out these functions, are stored in a memory (not shown) that is accessible to controller 56.

In some embodiments, motion controller 56 operates in the same or similar manners to the main microcontroller 58 and its associated circuitry disclosed in commonly assigned U.S. Pat. No. 10,420,687 issued Sep. 24, 2019, to inventors Aaron Furman et al. and entitled BATTERY MANAGEMENT FOR PATIENT SUPPORT APPARATUSES, the complete disclosure of which is incorporated herein by reference. In such embodiments, motion controller 56 controls the sending of pulse width modulated (PWM) signals to the motors contained within actuators 58*a-d*, thereby controlling both the speed and the direction of movement of these actuators. Motion controller 56 may take on other forms as well.

Motion controller 56 is in communication with control panel 54 and receives signals from control panel 54 indicating when a user wishes to move one or more components of patient support apparatus 20. That is, control panel 54 includes one or more controls 78 that are adapted, when activated, to instruct motion controller 56 to carry out the desired movement of the various movable components of patient support apparatus 20, as well as one or more controls for stopping such motion. Such movement includes, but is not limited to, raising and lowering the height of litter frame 28, pivoting the Fowler section 44 up and down about a generally horizontal axis (extending laterally from one side of the patient support apparatus 20 to the other), and/or lifting and lowering a knee gatch on patient support apparatus 20.

Head end lift actuator 58*a* is configured to change the height of the head end 38 of litter frame 28. Foot end lift actuator 58*b* is configured to change the height of the foot end 40 of litter frame 28. When both of these actuators 58*a* and 58*b* are operated simultaneously and at the same speed, the height of litter frame 28 is raised or lowered without changing the general orientation of litter frame 28 with respect to horizontal. When one or more of these actuators 58*a* and/or 58*b* are operated at different times and/or at different speeds, the orientation of litter frame 28 is changed with respect to horizontal. Lift actuators 58*a* and 58*b* are therefore able to tilt litter frame 28 to a variety of different orientations, including, but not limited to, a Trendelenburg orientation and a reverse-Trendelenburg orientation.

Gatch actuator 58*c* is adapted to raise and lower the joint that couples together the thigh section 46 and the foot section 48 of support deck 30, thereby raising and lowering the portion of the support deck 30 that is positioned close to the patient's knees. Fowler actuator 58*d* is adapted to raise and lower the head section (or Fowler section) 44 of the support deck 30.

Control panel 54 (FIG. 2) may be one of several control panels positioned on patient support apparatus 20. Although control panel 54 is show in FIG. 1 to be positioned on footboard 34, it will be understood that control panel 54 may be positioned at other locations, such as, but not limited to, on one or more of the siderails 36. Control panel 54 communicates with exit detection system 52 and motion controller 56 and includes a plurality of controls 78 that are adapted to control various aspects of patient support apparatus 20, including, but not limited to, exit detection system 52 and motion controller 56. The plurality of controls 78 may be implemented as buttons, dials, switches, icons on a touchscreen, or other devices. Control panel 54 also includes, in some embodiments, a display 80 for displaying information regarding exit detection system 52. Display 80 may be a touchscreen that displays one or more controls and/or one or more control screens, some of which are discussed in greater detail below. Display 80 may comprise an LED display, OLED display, or another type of display.

Control system 50 (FIG. 2) of patient support apparatus 20 also includes sensors 62-70, each of which is adapted to communicate information to exit detection system 52. Brake sensor 62 is adapted to detect if a brake onboard patient support apparatus 20 has been activated or not. When the brake is activated, one or more of wheels 24 are substantially prevented from moving, thereby rendering it difficult to move patient support apparatus 20 to different locations. Brake sensor 62 reports the status of the brake to exit detection system 52.

A/C power sensor 82 is adapted to detect whether or not patient support apparatus 20 is currently receiving electrical power from an A/C wall outlet, or if it is operating on battery power.

Battery charge sensor 64 detects the current charge level of one or more batteries positioned onboard patient support apparatus 20 (in those embodiments of patient support apparatus 20 that are configured to be able to operate on battery power). Battery charge sensor 64 reports this information to exit detection system 52.

Litter tilt angle sensor 66 detects the current angular orientation of litter frame 28 with respect to horizontal. Litter tilt angle sensor 66 detects this angle in the longitudinal direction along patient support apparatus 20 (e.g. in the direction from head end 38 to foot end 40, not in the side-to-side direction). Thus, litter tilt angle sensor 66 can be used to indicate whether litter frame 28 is in the Trendelenburg orientation, the reverse Trendelenburg orientation, or another orientation. In some embodiments, litter tilt angle sensor 66 detects the current angular orientation of litter frame 28 with respect to the base 22, rather than horizontal, in which case the output of sensor 66 will not vary when patient support apparatus 20 is positioned on an inclined or declined surface. In still other embodiments, litter tilt angle sensor 66 may comprise multiple sensors, such as, but not limited to, a first sensor that detects the angular orientation of litter frame 28 with respect to base 22 and a second sensor that detects the angular orientation of base frame 22 with respect to horizontal. Still other variations may be implemented, and regardless of the specific implementation, the output of the tilt sensor(s) are forwarded to exit detection system 52.

Fowler tilt angle sensor 68 detects the current angular orientation of Fowler section 44 with respect to horizontal (or, in some embodiments, with respect to the plane generally defined by litter frame 28 and/or the plane generally defined by support deck 30 when all of its sections are in a flat orientation). Fowler tilt angle sensor 68 reports its readings to exit detection system 52.

In some embodiments, one or both of litter tilt angle sensor 66 and/or Fowler tilt angle sensor 68 comprise position feedback sensors that are built into one or more of the actuators 58a, 58b, and/or 58d. In such embodiments, the sensors 66 and/or 68 may comprise Hall Effect sensors, encoders, and/or switches built into the actuators 58a, 58b and/or 58d that indicate the position of the extendable arm of the linear actuators. From this information, the angle of litter frame 28 and/or Fowler section 44 can be determined (such as by motion controller 56 and/or exit detection controller 72). Examples of such switches, sensors, and/or encoders are disclosed in the aforementioned commonly assigned U.S. patent application Ser. No. 15/449,277 filed Mar. 3, 2017, by inventors Anish Paul et al. and entitled PATIENT SUPPORT APPARATUS WITH ACTUATOR FEEDBACK, which is incorporated herein in its entirety.

Siderail position sensors 70 detect the position of each of the siderails 36 (up, down, or some other intermediate position) and report the positions of each of the siderails 36 to exit detection system 52.

All of the sensors 62-70 and 82 are adapted to communicate their information to exit detection system 52 which, as will be discussed in more detail below, may be configured to use some or all of this information when arming and/or changing a mode of operation of exit detection system 52.

Transceiver 60 (FIG. 2) is adapted to communicate with one or more devices positioned off-board patient support apparatus 20, such as, but not limited to, a hospital's local area network. In some embodiments, transceiver 60 is a conventional WiFi transceiver (i.e. IEEE 802.11 . . . ) adapted to wirelessly communicate with one or more wireless access points 84 of a hospital's local area network 86. In other embodiments, transceiver 60 may be a conventional Ethernet transceiver electrically coupled to a conventional Ethernet port (i.e. RJ-45 jack, or the like) built into patient support apparatus 20 that allows a conventional Ethernet cable to be coupled to the patient support apparatus 20. In these embodiments, patient support apparatuses 20 may be coupled to the hospital's local area network 86 by a wired connection. In still other embodiments, patient support apparatus 20 may have both wired and wireless transceivers 60. Still further, in some embodiments, transceiver 60 may take on a different form (e.g. a wireless ZigBee transceiver, a Bluetooth transceiver, etc.).

Patient support apparatus 20 uses transceiver 60, in some embodiments, to communicate with a patient support apparatus server 88. Patient support apparatus server 88 may be adapted to receive status information from patient support apparatuses 20 and distribute that information to one or more other servers and/or other devices coupled to local area network 86. In at least one embodiment, patient support apparatus server 88 includes a caregiver assistance application 90 that is adapted to communicate information between both patient support apparatuses 20 and one or more portable electronic devices 92. The portable electronic devices 92 includes, but are not limited to, smart phones, tablets, laptops, Computers on Wheels (COWs), and the like. Each portable electronic device 92 includes a display 94 on which one or more of the screens discussed in more detail below may be displayed. In some embodiments, caregiver assistance application 90 allows authorized users to remotely configure and remotely control various aspects of the exit detection system 52 of patient support apparatuses 20 using their portable computing device 92. In some of such embodiments, caregiver assistance application 90 may be configured to operate in the same manner as, and/or may be configured to include any of the same functionality as, the caregiver assistance application disclosed in commonly assigned U.S. patent application Ser. No. 62/868,947 filed Jun. 30, 2019, by inventors Thomas Durlach et al. and entitled CAREGIVER ASSISTANCE SYSTEM, the complete disclosure of which is incorporated herein by reference. In such embodiments, patient support apparatuses 20 may include any of the components and/or functionality of the patient support apparatuses disclosed in the aforementioned '947 application; portable computing devices 92 may include any of the components and/or functionality of the electronic devices 104a and/or 104b disclosed in the aforementioned '947 application; and caregiver assistance application 90 may communicate with any one or more of the servers disclosed in the aforementioned '947 application.

Figure 3:
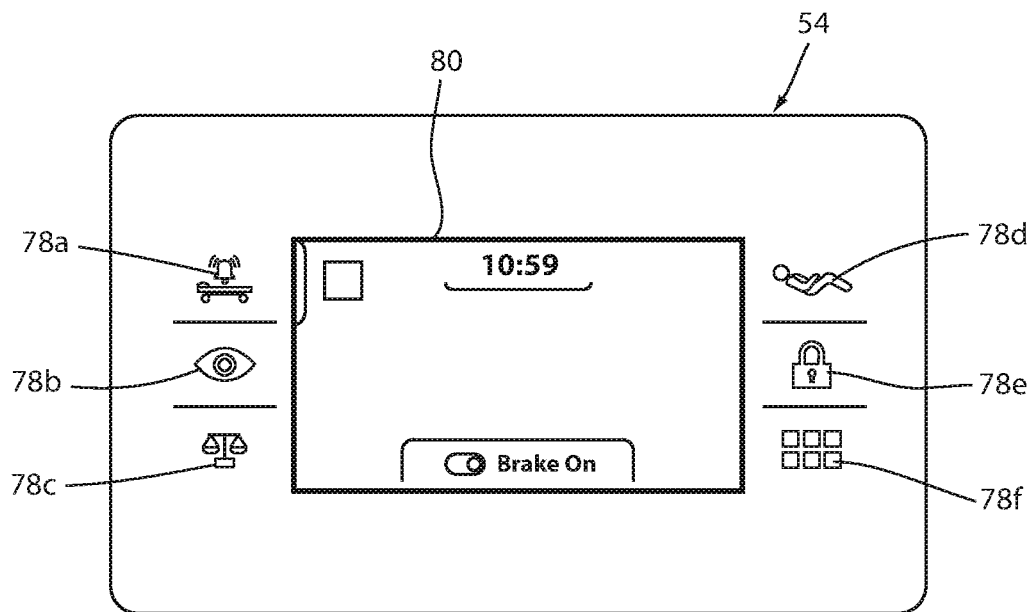
FIG. 3 is a plan view of a control panel of the patient support apparatus of FIG. 1.

One example of control panel 54 is shown in FIG. 3. In this example, control panel 54 includes six dedicated controls 78a-f, three of which are positioned to the left of display 80 and three of which are positioned to the right of display 80. Control 78a is configured, when pressed, to bring up an exit control screen that enables the user to control various aspects of exit detection system 52. Although control panel 54 is shown as including a dedicated control 78a for accessing the exit detection system 52 of patient support apparatus 20, it will be understood by those skilled in the art that display 80, which is a touchscreen in the examples disclosed herein, may include one or more icons that, when touched, allow the user to access controls for exit detection system 52. In other words, exit detection system 52 may be accessed via one or more touch screen controls in at least some alternative embodiments. In still other embodiments, a user may be able to access controls for the exit detection system 52 via both one or more dedicated controls and one or more touch screen control icons.

Figure 4:
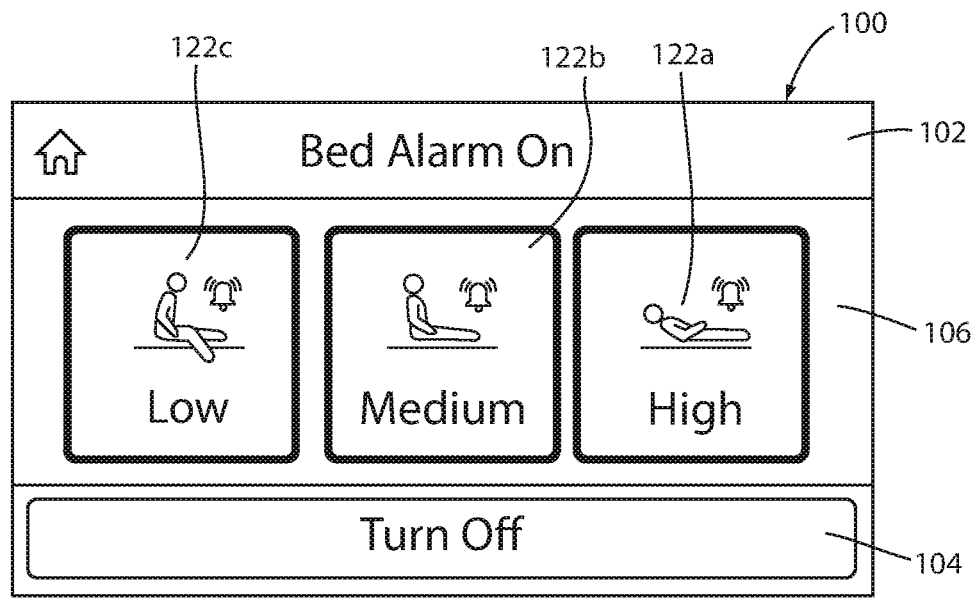
FIG. 4 is an exit detection arming screen displayable on the control panel of the FIG. 4.

FIG. 4 illustrates one example of a bed exit arming screen 100 that is displayable on display 80 of control panel 54. In some embodiments, arming screen 100 is displayed automatically in response to a user pressing exit detection control 78a. In other embodiments, arming screen 100 may be displayed in response to other triggers and/or be accessed by a user in other manners. Regardless of how accessed, bed exit arming screen 100 includes an upper status bar 102 indicating (in this example) that exit detection system 52 is currently armed; a lower control bar 104 that, when touched, allows a user to disarm exit detection system 52; and a mode indicator region 106 that indicates what user-selectable mode the exit detection system 52 is capable of operating in (as well what mode, if any, it is currently operating in).

In the embodiment discussed herein, exit detection system 52 is configured to operate in three user-selectable modes. It will be understood, however, that exit detection system 52 may be configured to operate in fewer user-selectable modes or a greater number of user-selectable modes, and that the following description of three user-selectable modes is merely for purposes of illustrating the principles of the present disclosure.

Each of the user-selectable modes of exit detection system 52 correspond to different sensitivity levels of exit detection system 52. These sensitivity levels refer to the relative freedom of movement of the patient when positioned on support deck 30. That is, a user-selectable mode with a higher sensitivity level means that exit detection system 52 will issue an exit alert when the patient moves by a relatively small amount toward either side of the patient support apparatus 20 (and/or, in some embodiments, toward the head end 38 and/or the foot end 40 of patient support apparatus 20). When exit detection system 52 operates in a user selectable mode with a medium sensitivity level, the patient is free to move closer to the sides and/or ends of the patient support apparatus 20 than he or she is able to do so with the high sensitivity level without exit detection system 52 issuing an exit alert. When exit detection system 52 operates in a user-selectable mode with a low sensitivity level, the patient is the most free to move toward the sides and/or ends of the patient support apparatus without triggering an exit detection alert.

In some embodiments, controller 72 determines the amount of movement toward the sides or ends of the patient support apparatus that trigger an exit alert by calculating relative changes in weight on force sensors 74. In such embodiments, force sensors 74 are positioned at different locations (such as adjacent four corners of the support apparatus) and exit detection system 52 triggers an exit alert when the ratio of forces detected on one end versus the other end, or the ratio of forces detected on one side versus the other side, change by more than a threshold. In these embodiments, the threshold changes based on the user-selected sensitivity. That is, if the user selects a mode of operation with the most sensitivity, then the smallest pre-programmed threshold is selected, and relatively small changes in the ratio of forces triggers an exit alert. If the user selects a mode of operation having a medium sensitivity level, a higher threshold than that used with the highest sensitivity level is used. And if the user selects a mode of operation having a high sensitivity level, the highest pre-programmed threshold level is used.

In other embodiments, such as will be described in more detail below, exit detection system 52 uses force sensors 74 to determine a center of gravity of the occupant in order to determine if the occupant is about to exit patient support apparatus 20, and thus issue an exit alert. In these center-of-gravity determining embodiments, exit detection system 52 may be configured to determine the center of gravity of the patient using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, other algorithms for determining the center of gravity may be used.

Figure 5:
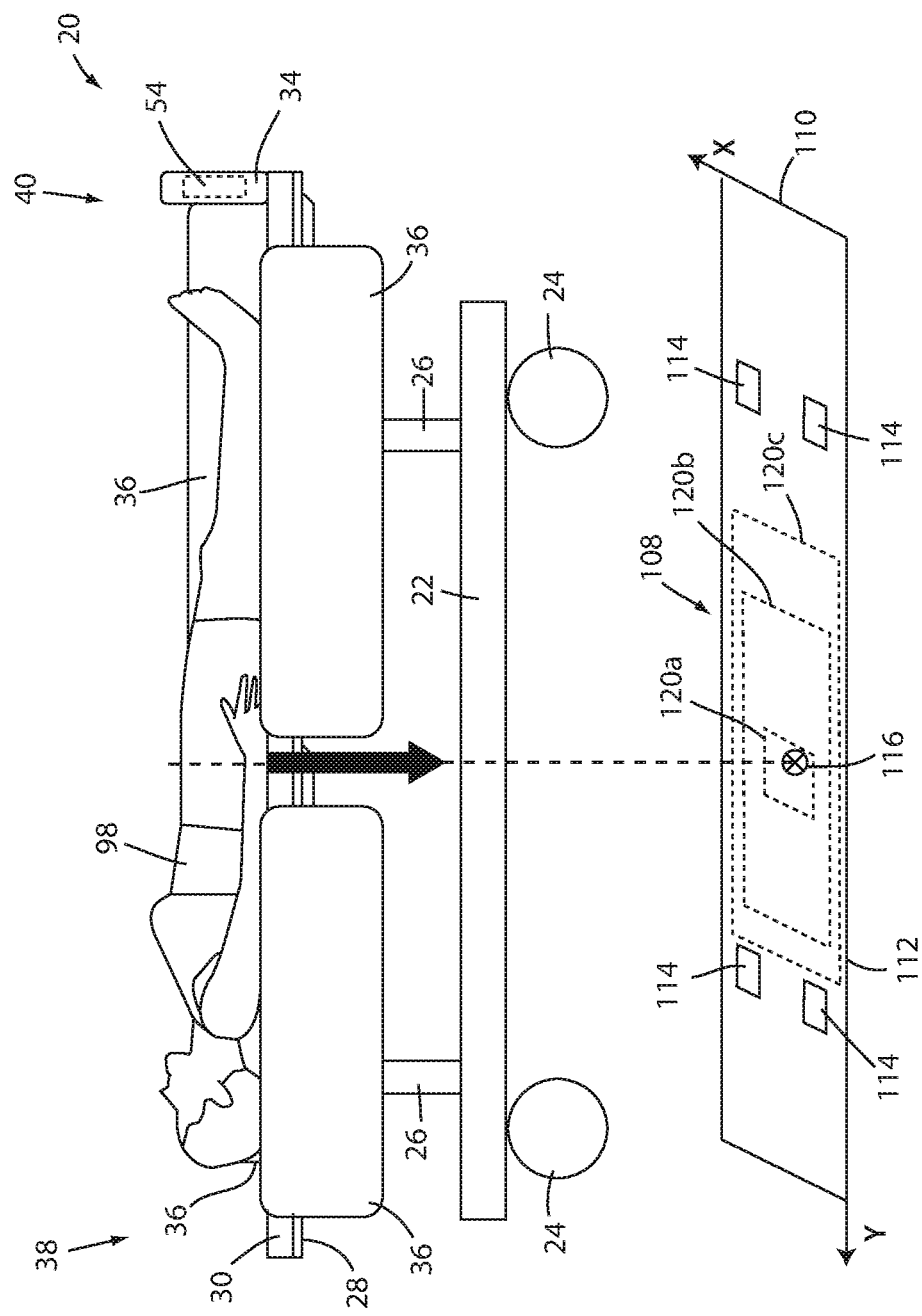
FIG. 5 is a diagram illustrating a reference frame for the patient support apparatus of FIG. 1 and the manner in which multiple user-selectable modes of the exit detection system map to the reference frame.

As shown more clearly in FIG. 5, controller 72 determines the center of gravity of the patient 98 in a planar coordinate frame of reference, such as reference frame 108. The plane of reference frame 108 is oriented generally parallel to the plane of litter frame 28 (e.g. it is horizontal when patient support apparatus 20 is supported on a horizontal surface and litter frame 28 is not tilted). Reference frame 108 includes an X-axis 110 and a Y-axis 112. X-axis 110 extends laterally in a direction generally parallel to a horizontal line extended from one side of the footboard 34 to the other side of the footboard 34 of patient support apparatus 20. Y-axis 112 extends longitudinally in a direction generally parallel to a line extending from head end 38 toward foot end 40 of patient support apparatus. Other frames of reference and/or coordinate systems can be used. Regardless of which frame of reference and/or coordinate system is used, exit detection controller 72 knows the location of force sensors 74 in the particular frame of reference and coordinate system used by the patient support apparatus 20. In the example shown in FIG. 5, force sensors 74 are shown in known locations 114.

Figure 8:
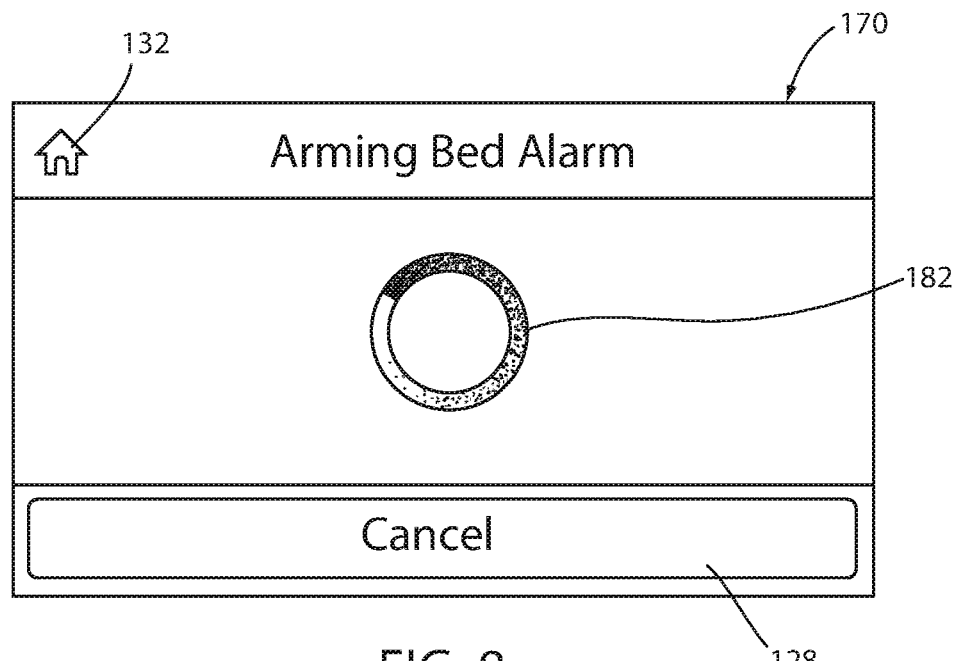
FIG. 8 is an exit detection arming screen displayable on the control panel of FIG. 4.

In the illustrative example shown in FIG. 8, controller 72 has determined the occupant's center of gravity to be at a location 116. When exit detection system 52 is armed, controller 72 compares this center of gravity 116 to one of multiple alert zones 120a-c. The particular alert zone 120a-c to which the patient's center of gravity 116 is compared depends upon which sensitivity level (i.e. which mode) the user has selected, as will be discussed in more detail below. Each zones 120a-c is defined in reference frame 108 and controller 72 determines whether the center of gravity 116 is inside or outside of whichever alert zone 120 is active (i.e. whichever one corresponds to the sensitivity level selected by the user). If center of gravity 116 moves outside of the active alert zone 120, controller 72 issues an alert indicating that the occupant is about to exit from patient support apparatus 20. The boundaries of alert zones 120a-c therefore define thresholds for the degree of movement of a patient that will trigger an exit alert by exit detection system 52.

When determining whether the center of gravity 116 is outside or inside of the active alert zone 120, controller 72 may first compute the center of gravity in a first one of the directions of coordinate frame of reference 108 (X direction or Y direction), compare that value to the corresponding boundaries of the zone in that particular direction and, if it is inside the boundaries, compute the center of gravity in the other direction of coordinate frame of reference 108 (X direction or Y direction). Alternative methods for determining whether the patient's current center of gravity 116 is currently within or outside of the active zone 120 may also be used.

As shown in FIG. 5, there are three different alert zones 120a, *b*, and *c*. Alert zones 120a, *b*, and *c* have different sizes, allowing the occupant to engage in different amounts of movement prior to triggering an exit alert. A user selects which one of the alert zones 120a-c will be the active alert zone using control panel 54. As discussed more below, this selection may be carried out by touching (or otherwise activating) one of the three sensitivity icons 122a-c shown on bed exit arming screen 100 in mode indicator region 106 (see FIG. 4). After a user has armed exit detection system 52 and selected the desired sensitivity level, controller 72 repetitively recalculates the occupant's center of gravity 116 based upon the outputs from force sensors 74 and compares the calculated center of gravity 116 to the active zone. If the center of gravity 116 is within the active alert zone 120, no exit alert is issued. If the center of gravity 116 moves outside of the active zone 120, controller 72 issues an alert. In some embodiments, in order to avoid issuing an alert based upon transient weight signals shifting the center of gravity 116 outside of the active zone 120 for a fleeting moment, controller 72 only issues an alert if the center of gravity 116 moves outside of the active zone 120 for more than a threshold amount of time (which may be on the order of seconds or a fraction of a second).

In the example shown in FIG. 5, alert zone 120a has the smallest area and corresponds to the most sensitive level for exit detection system 52. Alert zone 120b has a larger area than zone 120a and corresponds to a medium sensitivity level for exit detection system 52. Alert zone 120c has the largest area of all of the zones 120 and corresponds to the least sensitive level. The size of the alert zones 120 in frame of reference 108 therefore corresponds to the amount of freedom that the patient has to move toward the sides and/or ends of patient support apparatus 20 before an exit alert is issued by exit detection system 52.

In at least one embodiment, a user is able to select which alert zone 120a-c exit detection system 52 uses for determining whether or not to issue an exit alert (i.e. the active zone) by pressing on one of the three sensitivity icons 122a-c shown on display 80 of control panel 54 (see FIG. 4). If the user selects the high sensitivity icon 122a, exit detection system 52 uses zone 120a as the active zone. If the user selects medium sensitivity icon 122b, exit detection system 52 uses zone 120b as the active zone. And if the user selects low sensitivity icon 122c, exit detection system 52 uses zone 120c as the active zone.

It will be understood by those skilled in the art that the particular size and shape of the alert zones 120a-c shown in FIG. 5 are merely illustrative examples, and that the size and shape of these alert zones may vary in different embodiments. Further, as will be discussed more below, in some embodiments, patient support apparatus 20 may be configured to dynamically adjust the size and/or shape of these alert zones 120 during operation of patient support apparatus 20, such as when one or more components on patient support apparatus 20 move to a different position and/or orientation that indicate a greater or lesser likelihood of a patient exiting (e.g. siderails 36 are raised or lowered); when one or more components on patient support apparatus 20 move in a manner that changes the center of gravity calculation (e.g. litter frame 28 changes its tilt); when an object is added or removed from litter frame 28; and/or when one or more other changes are made that desirably lead to different size and/or shaped zones 120 (e.g. when patient support apparatus 20 is configured with a variable width support deck 30 and the width of support deck 30 is changed). Still other factors may be used to dynamically adjust the boundary of one or more zones 120.

Depending upon which sensitivity level the user selects, control panel 54 is configured to display the selected zone in a different manner than the other zones on the bed exit arming screen 100 (FIG. 4). This different manner may involve displaying the selected (i.e. active) zone in a different color; highlighting the selected zone; changing a background of the selected zone; adding a check mark or some other graphic to indicate the selection; and/or some other changes or combination of changes that visually identify which zone is the currently selected zone 120. In the example shown in FIG. 4, the user has selected the medium sensitivity level and control panel 54 indicates this selection by displaying sensitivity icon 122b with is different background color than it displays sensitivity icons 122a and 122c.

As will be discussed in greater detail below, exit detection system 52 is adapted to allow a user to switch between these sensitivity levels while a patient is positioned on patient support apparatus 20. To switch sensitivity levels, the user brings up bed exit arming screen 100 and touches one of the sensitivity level icons 122 that is currently not the active sensitivity level. When the user performs this switching, exit detection system 52 is configured to enter into a temporary transition mode in which it operates in a different manner from how it normally operates when operating with any of the three sensitivity levels shown in FIG. 4. This temporary transition mode continues while exit detection system 52 performs one or more transition tasks that are necessary for the system to switch to the newly selected sensitivity level. The temporary transition mode terminates automatically when any one of the following occurs: the exit detection system 52 successfully changes to the newly selected sensitivity level, the exit detection system is unable to change to the newly selected sensitivity level and the user gives up trying to make that switch; and/or the user cancels trying to make the switch to the new sensitivity level. The operation of exit detection system 52 in the transition mode is described in greater detail below.

In addition to temporarily operating in a transition mode when a user changes between sensitivity levels of exit detection system 52, exit detection system 52 is also configured to operate in the transition mode whenever it is initially armed. Still further, in some embodiments, exit detection system 52 is configured to operate in a motion mode when any one or more components on patient support apparatus 20 are being moved, such as, but not limited to, any movement caused by powered actuators 58a-d. The motion mode, like transition mode, is only temporary and lasts for as long as the movement of any one of the components of patient support apparatus 20 continues. Both the transition modes and the motion modes are described in more detail below with respect to FIG. 6.

In some embodiments, the motion modes are only executed when one or more components of patient support apparatus 20 are being moved for which real time information about the position of the moving component is available. In other words, those components for which only two positions, or small number of positions, are detected by a sensor do not trigger the motion mode. Instead, only movement of components, such as those moved by powered actuators 58a-d, which include position sensors that detect numerous positions the actuator 58a-d (and its moved component(s)), trigger a motion mode. For those components, such as, for example, siderails, for which only a raised position, a lowered position (and/or perhaps an intermediate position) are detectable, controller 72 may be programmed to remain in its current mode of operation (and not switch to a motion mode) when these components move. Thus, in some embodiments, controller 72 is programmed to enter a motion mode when a component moves whose position can be determined at multiple locations throughout its course of movement, and to not enter a motion mode when a component moves whose position is not detectable between its starting position and its ending positon (or is only detectable at, for example, a single intermediate position). Stated in another manner, a motion mode is only entered in some embodiments when real time feedback is available regarding the position of the moving component (or components).

FIG. 6 illustrates a plurality of different operational modes of one embodiment of patient support apparatus 20. These modes are classified according to whether they are selectable by a user, or whether they are automatically implemented by exit detection system 52 in response to a triggering event. The user selectable modes include a first mode 130a, a second mode 130b, and a third mode 130c. The automatic modes include a transition mode 134a or 134b and a motion mode 136a, 136b, or 136c. Although FIG. 6 illustrates two transition modes 134a and 134b, it will be understood that patient support apparatus, in most embodiments, will only be configured with the ability to use one of these transition modes 134, and that the two modes are shown in FIG. 6 merely for purposes of illustrating different manners of implementing the transition modes 134. Similarly, although FIG. 6 illustrates three motion modes 136a-c, this too is done merely for purposes of illustrating several different manners in which motion mode 136 may be implemented. In a typical patient support apparatus 20, exit detection system 52 will be configured to utilize only one of these modes 136.

FIG. 6 illustrates various functional aspects of exit detection system 52 when it is operating in each of the modes 130, 134, and/or 136. For example, when operating in mode 130a, exit detection system 52 repetitively calculates the center of gravity (C.O.G.) of the patient and determines if the center of gravity 116 is currently located outside of a first one of the alert zones 120. If it is, it issues an exit alert. When operating in second mode 130b, exit detection system 52 repetitively calculates the patient's center of gravity 116 and determines if it is currently located outside of a second one of the alert zones 120. If it is, it issues the exit alert. When operating in the third mode 130c, exit detection system 52 repetitively calculates the patient's center of gravity 116 and determines if it is currently located outside of a third one of the alert zones 120. If it is, it issues the exit alert.

The three user-selectable modes 130a-c (FIG. 6) correspond to the three different sensitivity levels which a user may select for operation of exit detection system 52. That is, if the user selects the lowest sensitivity level icon 122c on screen 100 (FIG. 4), exit detection system 52 will operate in a first one of the three modes 130a-c; if the user selects the medium sensitivity level icon 122b on screen 100 (FIG. 4), exit detection system 52 will operate in a second one of the three modes 130a-c; and if the user selects the highest sensitivity level icon 122a on screen 100 (FIG. 4), exit detection system 52 will operate in a third one of the three modes 130a-c. The particular mode 130a-c that corresponds to the particular one of the sensitivity level icons 122a-c does not matter because the modes 130a-c have been labeled generically with "first," "second" and "third" labels. Thus, in some embodiments, first mode 130a may correspond to highest sensitivity level icon 122a, in which case exit detection system 52—when operating in this mode—compares the patient's center of gravity 116 to alert zone 120a, and if the center of gravity 116 moves outside of the boundary of this alert zone 120a, it issues the exit alert. Alternatively, first mode 130a may correspond to lowest sensitivity level icon 122c, in which case exit detection system 52— when operating in this mode—compares the patient's center of gravity 116 to alert zone 120c, and if the center of gravity 116 moves outside of the boundary of this alert zone 120c, it issues the exit alert.

As can be seen from FIG. 6, in each of the three user-selectable modes 130a-c, exit detection system 52 is configured to issue the exit alert if the total weight of the patient detected by the exit detection system 52 decreases by fifty percent or more. Exit detection system 52 determines the total weight of the patient by summing the outputs from the force sensors 74 and subtracting the tare weight (which may be determined when no patient is present on patient support apparatus 20). If this patient weight decreases by fifty percent of more, exit detection system 52 issues an exit alert, even if the patient's center of gravity remains inside of the boundaries of the currently active alert zone 120.

It will be understood that the threshold for issuing the exit alert based on a reduction in the detected patient weight may be varied from fifty percent. In some embodiments, alert modes 130a-c are configured to issue this alert when the patient's detected weight decreases by ten percent or more. In other embodiments, other thresholds may be used. Regardless of the specific threshold used, the alert is based on a reduction in weight that occurs over a relatively short time (e.g. within seconds), not a reduction in weight that may occur over the course of days or weeks. In other words, the threshold is based on a reduction in the patient weight that would be expected to occur in the time span it might take a patient to climb out of patient support apparatus 20 in a manner that didn't involve moving his or her center of gravity outside of the active alert zone 120 (e.g. by grabbing onto an overhead support, partially or wholly supporting oneself on an overbed table or other equipment, or in some other manner).

It can be seen from FIG. 6 that the only difference in the operation of exit detection system 52 in the three user-adjustable modes is the particular zone whose boundaries exit detection system 52 is comparing the patient's center of gravity 116 to. That is, in one of the modes 130, exit detection system 52 compares the patient's center of gravity 116 to the boundaries of alert zone 120a; in another mode 130, it compares the patient's center of gravity 116 to the boundaries of alert zone 120b; and in another mode 130, it compares the patient's center of gravity 116 to the boundaries of alert zone 120c. In all of the modes 130a-c, it issues an alert if the patient's center of gravity 116 strays outside of the boundaries of whichever zone 120a-c is active, or if the patient's detected weight drops in a relatively short period of time by more than a threshold.

The automatic modes 134a-b and 136a-c shown in FIG. 6 are automatically implemented by exit detection system 52 in response to one or more triggering conditions. In one embodiment, the triggering condition for operating in transition modes 134a or 134b is the changing of a sensitivity level of exit detection system 52. That is, exit detection system 52 automatically operates in one of transition modes 134a or 134b whenever the user switches from one sensitivity level to another sensitivity level (i.e. whenever the user changes from one of the modes 130 to different one of the modes 130). In some embodiments, exit detection system 52 may include a second triggering condition; namely, when exit detection system 52 is initially armed. In such embodiments, exit detection system 52 is also configured to automatically operate in one of transition modes 134a or 134b whenever a user switches the exit detection system 52 from a disarmed state to an armed state.

Exit detection system 52 is further configured to automatically switch out of operating in the transition mode 134 when one of the following occurs: exit detection system 52 successfully arms itself with the new sensitivity level, exit detection system 52 is unable to arm itself with the new sensitivity level and the user abandons attempts to switch to the new sensitivity level, or the user cancels the attempt by exit detection system 52 to arm itself with the new sensitivity level. These events will be explained in greater detail below. When exit detection system 52 is unable to transition to the new sensitivity level (or the user cancels the attempt), exit detection system 52 is configured to automatically return to the mode 130 it was previously operating in, or if it was not previously armed, to return to the disarmed state.

The triggering event for exit detection system 52 to operate in one of the motion modes 136a-c is any movement of a component of patient support apparatus 20 that affects the center of gravity calculations of exit detection system 52 and whose position can effectively be continuously determined throughout the movement of the component by one or more sensors on board patient support apparatus 20. Generally speaking, this corresponds to any movement by any of powered actuators 58a-d, although exit detection system 52 may be configured to automatically switch to a motion mode 136 based on other movement for which appropriate continuous position sensors are provided. Thus, for example, in those embodiments of patient support apparatus 20 that include siderail position sensors that are only capable of detecting the raised and lowered position of the siderails 36 (and not dozens or more of their intermediate positions), controller 72 does not switch to a motion mode in response to movement of the siderails. Similarly, in those embodiments of patient support apparatus 20 that have expandable decks (width-wise, lengthwise, and/or both) with sensors that only detect when the deck has been moved to one of its two or three predetermined positions (e.g. a contracted position, an expanded position, etc.), controller 72 does not switch to a motion mode in response to the motion made during the transition between these predetermined positions. In contrast, when one of powered actuators 58a-d moves, controller 72 switches to a motion mode because the actuators 58a-d include sensors (such as Hall effect and/or encoders, etc.) that tell controller 72 the position of these actuators (and/or the components they drive) substantially continuously throughout their movement. The triggering event for exit detection system 52 to stop operating in the motion mode 136 is the cessation of the movement that triggered motion mode 136.

When exit detection system 52 is operating in first transition mode 134a, it continues to calculate a center of gravity 116 of the patient. It also compares the center of gravity to the boundary of a zone 120 to determine whether the center of gravity is inside or outside of that zone 120. The particular zone that exit detection system 52 uses in the transition mode 134a is whichever zone 120 has the least sensitivity. The boundaries of this least sensitive zone 120 define a transition threshold that, if crossed by the patient's center of gravity 116 during the transition mode, triggers an exit alert.

In the example shown in FIG. 5, the transition zone corresponds to zone 120c. Thus, in that example, when exit detection system 52 starts operating in transition mode 134a, it automatically switches to using zone 120c, to the extent zones 120c was not the active zone immediately prior to entering transition mode 134a. To the extent zone 120c was the active zone immediately prior to entering transition mode 134a, exit detection system 52 continues to utilize zone 120c during the transition mode.

In some embodiments, exit detection system 52 is configured to use a zone 120 during transition mode 134a that has less sensitivity than any of the three zones 120 used in the user-selectable modes 130a-c. In such embodiments, exit detection system 52 automatically switches to using an active zone that has a larger area than zone 120c (FIG. 5) while operating in the transition mode.

While operating in transition mode 124a, exit detection system 52 continues to monitor the weight of the patient and to check for relatively rapid decreases in the patient's weight that are indicative of a patient exiting the patient support apparatus 20. That is, it continues to look for weight decreases that exceed a particular threshold. In the example shown in FIG. 6, exit detection system 52 uses a threshold of fifty percent in all of the modes 130a-c, 134a-b, and 136a-c. It will be understood, however, that other thresholds may be used for any one or more of these various modes.

When exit detection system 52 operates in second transition mode 134b, exit detection system 52 ceases to issue alerts based on whether or not the patient's center of gravity 116 falls outside of an active zone 120. Instead, it only issues an exit alert while in transition mode 134b if it detects a reduction in patient weight of more than a threshold (e.g. fifty percent). In some embodiments, exit detection system 52 ceases the calculation of the patient's center of gravity 116 while in transition mode 134b. In other embodiments, exit detection system 52 continues to calculate the patient's center of gravity, but does not compare it to any zone 120 while in transition mode 134b. In still other embodiments, exit detection system 52 continues to both calculate the patient's center of gravity 116 and compare it to an active zone while in transition mode 134b, but exit detection system 52 does not issue any exit alert if the patient's center of gravity 116 strays outside of the active zone 120. Thus, in all of these various embodiments, exit detection system 52 only issues an exit alert if the patient's weight decreases by more than the threshold.

As was noted previously, patient support apparatus 20, in most embodiments, is programmed to only use one of the transition modes 134a or 134b, and these two modes have been illustrated and described herein merely to provide examples of the types of transition modes 134 that exit detection system 52 is capable of implementing.

Whenever exit detection system 52 enters a transition mode 134a or 134b, it also attempts to perform at least one transition task that is necessary for the exit detection system 52 to initially arm itself and/or that is necessary for the exit detection system 52 to transition to a different sensitivity level. Such transition tasks may vary, and in some embodiments, exit detection system 52 is configured to perform multiple such transition tasks. In many embodiments, exit detection system 52 is configured to notify the user if it is unable to complete the necessary transition task(s) and to allow the user to either cancel the change in sensitivity (or cancel the arming of the exit detection system 52 if it wasn't previously armed), or to retry the one or more transition tasks. These content of these transition tasks is described in greater detail below.

Exit detection system 52 remains in transition mode 134a or 134b until at least one of the following occurs: (a) exit detection system 52 is able to complete all of the necessary transition tasks, and it therefore transitions to operating with the new sensitivity level (i.e. it begins operating with whichever one of modes 130a-c that corresponds to the new sensitivity level); (b) exit detection system 52 is unable to complete at least one of the transition task(s) and the user doesn't instruct the exit detection system 52 to retry or to cancel the transition task(s) within a predetermined time period; or (c) exit detection system 52 receives a cancel instruction from the user at some point while in the transition mode 134a or 134b. When exit detection system 52 exits the transition mode 134a or 134b in the first manner (occurrence (a)), it automatically switches to the mode 130a-c having the sensitivity level that corresponds to what the user selected. For example, if exit detection system 52 has entered a transition mode 134a or 134b because the user has pressed the high sensitivity icon 122a (FIG. 4), exit detection system 52 exits the transition mode by switching to the mode 130a-c that utilizes zone 120a as the active zone (FIG. 5). When exit detection system 52 exits the transition mode 134a or 134b in the second or third manners (occurrences (b) or (c)), it automatically returns to whichever mode it was operating in immediately prior to the user attempting to switch sensitivity levels (or, if the exit detection system 52 was not previously armed, it returns to the unarmed state).

When exit detection system 52 operates in motion mode 136a (FIG. 6), it stops calculating the patient's center of gravity 116, and thus stops issuing any alerts based on the patient's center of gravity straying outside of the boundaries of the active zone 120. Instead, exit detection system 52 only issues an exit alert while in motion mode 136*a* if the patient's weight decreases by more than a threshold within a short period of time. In addition, exit detection system 52 may be configured to change the boundary of one or more of the zones 120*a-c* upon exiting motion mode 136*a*. The changes made by exit detection system 52 to the boundary of one or more of zones 120*a-c* are based upon the movement that takes place while exit detection system 52 is operating in motion mode 136*a*. That is, exit detection system 52 adjusts the zone boundaries based upon not only which component(s) of patient support apparatus 20 have moved during the time it is operating in motion mode 136*a*, but also the extent and direction of the movement of each of those components.

The adjustments to the zone boundaries that exit detection system 52 is configured to make when it exits motion mode 136*a* are adjustments that, generally speaking, take into account changes in the calculated center of gravity 116 of the patient that are caused by the component(s)' movement, rather than movement of the patient. For example, the patient's calculated center of gravity 116*a* when the litter frame 28 is in the Trendelenburg orientation is positioned closer to the head end 38 of the patient support apparatus 20 than the foot end 40. However, the patient's calculated center of gravity 116*b* is positioned closer to the foot end 40 of the patient support apparatus when litter frame 28 is in the reverse Trendelenburg orientation. This change in position is not the result of any movement of the patient 98 because the position and orientation of the patient with respect to litter frame 28 is unchanged between the Trendelenburg and reverse Trendelenburg orientations. Accordingly, in some embodiments, exit detection system 52 is configured to change the position of zones 120*a-c* to accommodate this change in the patient's calculated center of gravity when it exits motion mode 136*a*.

Exit detection system 52 may be configured to make other changes to the size, shape, and/or position of zones 120*a-c* when it exits motion mode 136. Such other changes may be based on, for example, pivoting of Fowler section 44 about its horizontal axis. In some embodiments of patient support apparatus 20, lifts 26 may be configured to interact with litter frame 28 during raising and lowering of litter frame 28 in such a manner that the calculated center of gravity 116 changes at different heights of litter frame 28. In these embodiments, exit detection system 52 may be configured to make changes to the boundaries of one or more of the zones 120*a-c* in response to changes in the height of litter frame 28. The movement of still other components may be monitored during motion mode 136*a* and accounted for upon exiting motion 136*a* by changing the size, shape, and/or position of one or more alert zones 120*a-c*.

When exit detection system 52 operates in motion mode 136*b* (FIG. 6), it continues to calculate the patient's center of gravity 116, but stops issuing any alerts based on the patient's center of gravity straying outside of the boundaries of the active zone 120. That is, even if the patient's center of gravity 116 moves outside of the active zone, exit detection system 52 does not issue an alert in response to that movement outside of the zone. Instead, exit detection system 52 only issues an exit alert while in motion mode 136*b* if the patient's weight decreases by more than a threshold within a short period of time.

While in motion mode 136*b*, exit detection system 52 may also be configured to change the boundary of one or more of the zones 120*a-c* upon exiting motion mode 136*b*. The changes made by exit detection system 52 to the boundary of one or more of zones 120*a-c* are the same type of boundary changes discussed above with respect to motion mode 136*a*, and do not need to be repeated herein.

When exit detection system 52 operates in motion mode 136*c* (FIG. 6), it continues to calculate the patient's center of gravity 116, but it uses a dynamically changing active zone 120*a-c* whose boundaries it repetitively updates during the duration of motion mode 136*c*. That is, for example, if exit detection system 52 is operating in first mode 130*a* prior to switching to motion mode 136*c*, and the active zone 120 at that time is zone 120*b*, exit detection system 52 will dynamically change the boundaries of active zone 120*b* while in the motion mode. If the patient's center of gravity 116 moves outside of the dynamically changing boundary at any time while in motion mode 136*c*, exit detection system 52 issues an exit alert.

The changes that exit detection system 52 makes to the boundaries of zones 120*a-c* while operating in motion mode 136*c* are the same changes it makes to the boundaries of these zones when it leaves motion modes 136*a* or 136*b*, as discussed above. The only difference is that, while in motion mode 136*c*, exit detection system 52 makes the changes repetitively while the one or more components of patient support apparatus 20 are in motion, whereas, when in motion modes 136*a* or 136*b*, exit detection system 52 waits until exiting those motion modes before making the adjustments to zones 120*a-c*.

When exit detection system 52 is in motion mode 136*c* and the motion stops, it returns to whichever user-selectable mode 130 it was previously in and operates in that mode using the updated boundaries that it dynamically calculated while in mode 136*c*. Thus, for example, if exit detection system 52 repetitively shifts the zones 120*a-c* toward the head end of patient support apparatus 20 without changing their shape while in motion mode 136*c*, the most recent head-end-shifted set of boundaries that it calculated at the last moment it was operating in motion mode 136*c* will be used as the boundaries for whichever one of modes 130*a-c* it returns to.

For all of motion modes 136*a-c*, it will be understood that whatever changes to the size, shape, and/or position of the alert zones 120*a-c* that exit detection system 52 makes at the termination of, or during, operation of these motion modes, exit detection system 52 thereafter uses those adjusted zones 120*a-c* during the operation of modes 130*a-c*. The adjusted boundaries, in some embodiments, remain in place until exit detection system 52 re-enters a motion mode 136. After re-entering and re-exiting a motion mode, a revised set of boundaries for zones 120*a-c* are used. This process of revising the boundaries during, or immediately after, motion modes 136 and then maintaining the boundaries in a static form while in motion modes 130*a-c* continues for as long as exit detection system 52 remains armed.

For all of the motion modes 136*a-c*, further details regarding several manners in which exit detection system 52 may change the size, shape, and/or position of one or more of alert zones 120*a-c* are disclosed in commonly assigned U.S. patent application Ser. No. 62/889,254 filed Aug. 20, 2019, by inventors Sujay Sukumaran et al. and entitled PERSON SUPPORT APPARATUS WITH ADJUSTABLE EXIT DETECTION ZONES, and Ser. No. 15/266,575 filed Sep. 15, 2016, by inventors Anuj K. Sidhu et al. and entitled PERSON SUPPORT APPARATUSES WITH EXIT DETECTION SYSTEMS, the complete disclosures of both of which are incorporated herein by reference. Any of the adjustments disclosed in these patent applications may be made by exit detection system 52 for any of motion modes 136*a-c*, and such changes may be made either during the motion mode, or after exiting the motion mode.

As an alternative to making adjustments to the size, shape, and/or position of one or more alert zones 120 as part of motion modes 136*a-c*, exit detection system 52 may be configured to adjust the calculated center of gravity 116 of the patient to take into account that portion of the change in the center of gravity 116 that is due to the movement of the component(s) of the patient support apparatus 20. In these embodiments, exit detection system 52 may leave the boundaries of alert zones 120*a-c* unchanged when operating in motion modes 136*a-c*, but instead adjust the center of gravity 116 so that the effects of the component(s) movement on the center of gravity calculation 116 are stripped out of the calculation. For motion modes 136*a* and 136*b*, these adjustments may be delayed until exit detection exits these modes, while in motion mode 136*c*, these adjustments may be made dynamically as the component(s) of patient support apparatus 20 move. Several manners in which these adjustments to the center of gravity can be made are disclosed in commonly assigned U.S. Pat. No. 10,617,327 issued Apr. 14, 2020, to inventors Marko Kostic et al. and entitled EXIT DETECTION SYSTEM WITH COMPENSATION, the complete disclosure of which is incorporated herein by reference. The adjustments to the patient's calculated center of gravity may be made for movement of any of the actuators 58*a-d*, and/or for movement of other components of patient support apparatus 20.

In still other embodiments, exit detection system 52 is configured to not only adjust the size, shape, and/or position of one or more alert zones during, or after, motion modes 136*a-c*, it is also configured to adjust the patient's calculated center of gravity. Thus, for example, if the Fowler tilt angle increases during movement, the readings from each of the force sensors 74 are adjusted based on the known weight of the patient, and the known distribution of that weight on the force sensors 74 prior to the movement of the Fowler section (it is assumed that the patient does not move on the support deck during this movement). This adjustment changes the calculated center of gravity by effectively removing the shift in the patient's weight that is due to the raising of the Fowler (but does not remove shifts in the patient's weight due to his or her movement relative to the support deck—as discussed more in the aforementioned U.S. Pat. No. 10,617,327. The adjustment to the side, shape, and/or alert zone is also implemented in order to allow the patient an adjusted area of alert-free movement that betters matches his or her new orientation after the Fowler has been raised).

As with transition modes 134*a* and 134*b*, patient support apparatus 20, in most embodiments, is programmed to only use one of the motion modes 136*a*, 136*b*, or 136*c*. The illustration of three different motion modes 136*a-c* in FIG. 6 has been provided merely to illustrate examples of the types of motion modes 136 that exit detection system 52 is capable of implementing. Exit detection system 52 may be modified to utilize still other types of motion modes when movement of one or more components is detected. Still further, it will be understood that, in some embodiments, exit detection system 52 can be implemented with only a transition mode and no motion mode, while in other embodiments exit detection system 52 can be implemented with only a motion mode and no transition mode, while in still other embodiments, exit detection system 52 is implemented with both a motion mode and a transition mode.

Figure 7:
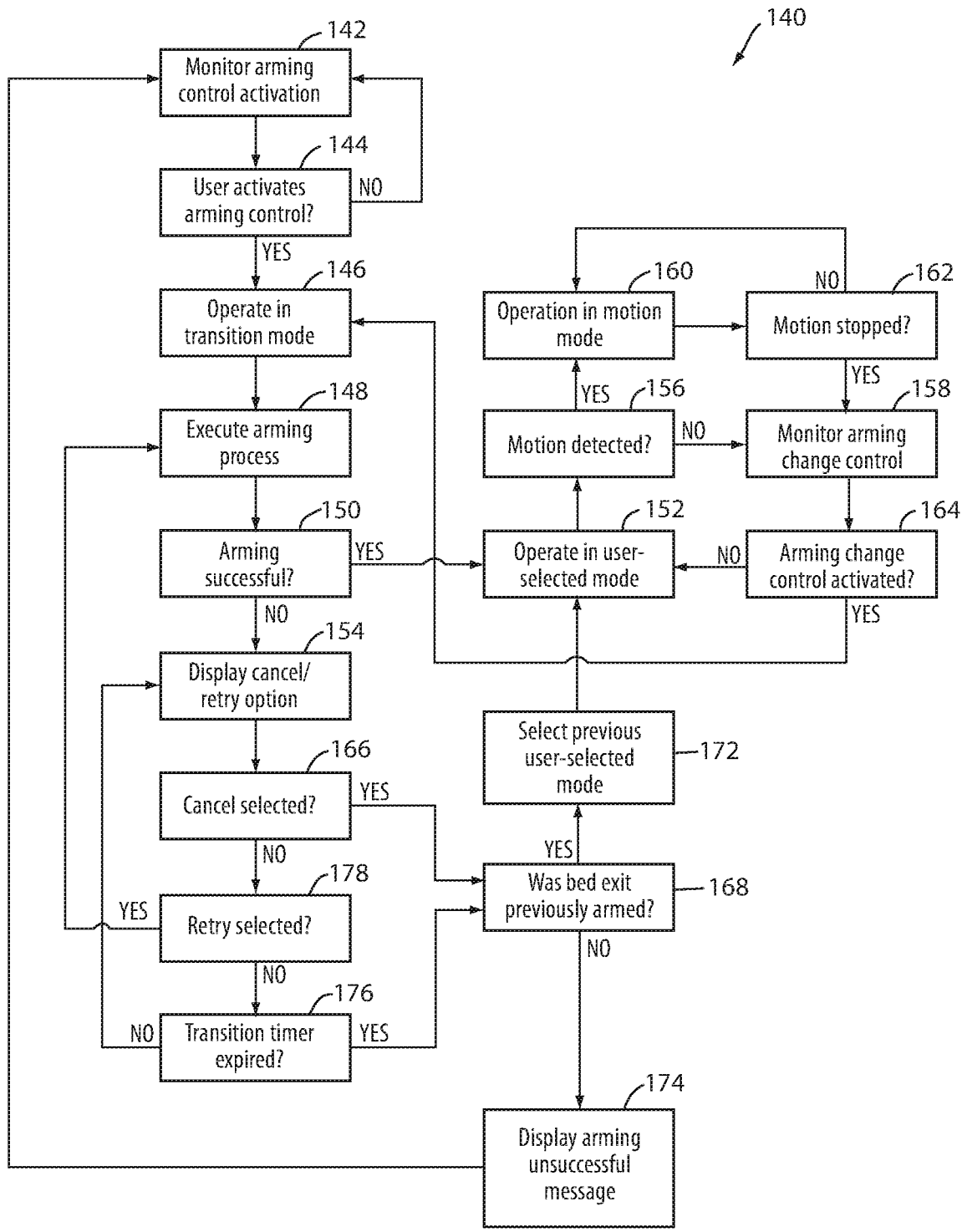
FIG. 7 is a flow chart illustrating an exit detection operation algorithm of the patient support apparatus of FIG. 1.

FIG. 7 illustrates an automatic mode selection algorithm 140 that is implemented by controller 72 of exit detection system 52 in an embodiment of the present disclosure. Mode selection algorithm 140 begins at a first step 142 where controller 72 monitors signals from control panel 54. More specifically, controller 72 monitors signals indicating that a user has pressed on the one or more controls (e.g. control 78*a*) that arm exit detection system 52 or that switch an already-armed exit detection system 52 from one sensitivity level to a different sensitivity level. At step 144, controller 72 determines if any such signals have arrived from control panel 54. If no such signals have arrived, controller 72 returns to step 142 where it continues to monitor outputs from control panel 54 for such signals. If controller 72 does receive a signal indicating the user has pressed a control (78*a*) to arm exit detection system 52 or change it sensitivity level, controller 72 proceeds from step 144 to step 146.

At step 146 (FIG. 7), controller 72 automatically switches exit detection system 52 into the transition mode in response to the user pressing arming control 78*a* (or a control to switch sensitivity levels). As was noted previously, controller 72 switches to transition mode 134*a* in some embodiments, while in other embodiments, it switches to transition mode 134*b*, while in still other embodiments, it may switch to still other types of transition modes 134.

After switching to a transition mode 134 at step 146, controller 72 moves onto step 148 where it begins an arming process. The arming process is executed both when exit detection system 52 is initially armed, as well as when exit detection system 52 is already armed but the user is attempting to switch its sensitivity level from a first level to another level. The arming process involves completing one or more transition tasks that are prerequisites for exit detection system 52 to arm itself, either initially or with a new sensitivity level. These transition tasks, in at least one embodiment, include the following: (a) confirming that a brake onboard patient support apparatus 20 is activated; (b) confirming that the bed is either plugged into an AC wall outlet, or, if operating on battery power, that a charge level of the battery is above a threshold; (c) confirming that a patient weight is detected onboard patient support apparatus (by force sensors 74) for a minimum amount of time; (d) confirming that the weight detected by force sensors 74 remains stable for a minimum amount of time; and (e) confirming that the calculated patient's center of gravity remains within the desired active zone 120*a-c* (or an arming zone) for a minimum amount of time.

The minimum amount of time used by controller 72 in carrying out transition tasks (c), (d), and (e) may vary. In some embodiments, this minimum amount of time is approximately 3-5 seconds. Other times—both greater and lesser—can, of course, be used. In addition, this minimum amount of time, may be the same for all of the transition tasks (c), (d), and (e), or one or more of the transition tasks (c), (d), and/or (e) may use a value for this minimum amount of time that is different from the minimum amount of time value used by one or more of the other transition tasks.

It will also be understood that both the number and content of the transition tasks may vary from the five identified above. In some embodiments, exit detection system 52 includes additional transition tasks, while in other embodiments, it includes fewer transition tasks. In those embodiments with additional transition tasks, such additional transition tasks may include any one or more of the following: (a) confirming that the scale system comprised of force sensors 74 has been calibrated; (b) confirming that the scale system has been zeroed; and/or (c) and confirming that footboard 34 is coupled to litter frame 28 (in some embodiments, footboard 34 is removable from litter frame 28).

In those embodiments of exit detection system 52 where a transition task includes confirming that a brake is activated, exit detection system 52 is configured to not arm itself (and/or to not be able to change sensitivity levels) when the brake is deactivated. In these embodiments, the failure to activate the brake leads to control panel 54 displaying a message reminding the caregiver to activate the brake, or otherwise indicating that exit detection system 52 cannot arm itself, or change sensitivity levels, while the brake is deactivated. These embodiments help remind the caregiver to activate the brake, which helps reduce the potential for patient falls when the patient exits from patient support apparatus 20.

In those embodiments of exit detection system 52 where a transition task includes confirming that patient support apparatus 20 is plugged into an AC wall outlet, or, if not, that its onboard battery has sufficient charge, exit detection system 52 communicates with both AC power sensor 82 and battery charge sensor 64. In these embodiments, patient support apparatus 20 may be configured to reduce certain functionality if operating on battery power and the battery drops below one or more threshold charge levels. In some of these embodiments, the reduced functionality based on the battery charge state takes on any of the forms disclosed in commonly assigned U.S. patent application Ser. No. 16/828,323 filed Mar. 24, 2020, by inventors Zane Shami et al. and entitled PATIENT CARE SYSTEM WITH POWER MANAGEMENT, the complete disclosure of which is incorporated herein by reference. In other embodiments, the functionality of exit detection system 52 in relation to the charge status of the battery may take on other forms.

In those embodiments of exit detection system 52 where a transition task includes confirming that a patient weight is detected onboard patient support apparatus (by force sensors 74) for a minimum amount of time, exit detection system 52 monitors the outputs from force sensors 74 for the minimum amount of time and confirms that the patient weight (total weight minus tare weight) is equal to or exceeds a minimum value. The minimum value is chosen low enough to encompass substantially all patients who might use patient support apparatus, but high enough so that it is unlikely to be satisfied by common items that might be expected to be present on litter frame 28 (e.g. bedding, pillows, equipment, etc.). Thus, for patient support apparatuses 20 intended to be used with adults, the minimum weight might be set at approximately fifty or seventy five pounds, although other weight values may, of course, be used. If patient support apparatus 20 is intended to be used with children, a smaller weight value might be used, such as, but not limited to ten, twenty, thirty pounds, or still other values.

In those embodiments of exit detection system 52 where a transition task includes confirming that the weight detected by force sensors 74 remains stable for a minimum amount of time, controller 72 monitors the outputs from force sensors 74 during the minimum amount of time and looks for changes that exceeds one or more thresholds. The thresholds may vary depending upon total patient weight and/or they may vary for one or more of the individual force sensors. However, implemented, the values are chosen such that the readings from force sensors 74 are stable enough to generate an accurate calculation of the patient's center of gravity during the minimum amount of time.

In those embodiments of exit detection system 52 where a transition task includes confirming that the calculated patient's center of gravity 116 remains within the desired active zone 120a-controller 72 calculates the patient center of gravity 116 repetitively during the minimum amount of time and compares it to the boundaries of the zone 120a-c that the user is attempting to arm exit detection system 52 with (either initially, or as a new sensitivity level). Controller 72 compares this center of gravity 116 with the boundaries of this desired active zone 120 and determines if the center of gravity 116 is within the zone or not. As will be discussed more below, if the center of gravity 116 does not remain within the desired active zone 120 for the minimum amount of time, controller 72 prevents exit detection system 52 from arming itself (either initially or with a new sensitivity level).

Returning to algorithm 140 (FIG. 7), controller 72 determines at step 150 whether all of the necessary transition tasks have been successfully completed for not. If they have not, it proceeds to step 152. If they have, it proceeds to step 154. For example, if controller 72 determines at step 150 that the brake is activated, that the bed is plugged into an AC wall outlet (or has sufficient battery power), that a patient weight has been detected from a minimum time, that the detected weight has remained stable for a minimum amount of time, and that the calculated patient's center of gravity 116 has remained within the desired active zone 120a-c for a minimum amount of time, it proceeds to step 152. If not, it proceeds to step 154.

Turning first to step 152, controller 72 begins operating in whichever mode 130a-c that the user had selected at step 144. That it, at step 152, controller 72 ceases to operate in the transition mode 134 and automatically switches to operating in whichever one of the modes 130a-c that the user had selected on control panel 54. While operating in this mode, controller 72 proceeds to step 156 where it determines if any movement is taking place. Controller 72 carries out this step via communication with motion controller 56 (FIG. 2). Motion controller 56 is configured, in some embodiments, to send a message to exit detection system 52 whenever it is driving any of powered actuators 58a-d. Such messages indicate not only that an actuator 58 is being driven, but they also indicate which specific actuator(s) 58 are being driven and in which direction (and in some embodiments, at what speed). In other embodiments, at noted previously, motion controller 56 and exit detection controller 72 may be combined into a single controller, in which case such messages are not needed. However configured, controller 72 is configured to proceed to step 158 if there is no motion of any components of patient support apparatus 20, as determined at step 156. On the other hand, controller 72 is configured to proceed to step 160 if it detects motion at step 156.

At step 160 (FIG. 7), controller 72 automatically enters one of motion modes 136a-c. As noted, the particular mode 136a-c entered by controller 72 depends upon the particular embodiment of patient support apparatus 20, and may vary from embodiment to embodiment. While in the motion mode 136, controller 72 carries out the motion tasks described above with respect to FIG. 6. The execution of the motion mode 136 continues until movement of all of the components of patient support apparatus 20 stops, as detected at step 162. More specifically, if controller 72 detects at step 162 that the movement of the component(s) has stopped, it automatically exits the motion mode 136 and proceeds to step 158. If movement still continues, it returns back to step 160 and remains in the motion mode.

Controller 72 arrives at step 158 in one of two manners, either in response to no motion being detected at step 156 or in response to motion terminating, as detected at step 162. In either case, controller 72 carries out step 158 while operating in whichever one of the user selected modes it was operating in at step 152. At step 158, controller 72 monitors the user control(s) 78 on control panel 54 that control one or more aspects of exit detection system 52. If one or more of these controls are activated at step 158, controller 72 determines at step 164 whether the user has activated a control that changes the sensitivity level of exit detection system 52 to a different sensitivity level. If the user has, controller 72 returns back to step 146, where it automatically begins to operate in a transition mode 134a-b, as described previously. If the user has not activated a sensitivity level change, controller 72 returns to step 152 where it continues to operate in its current user-selected mode 130.

Figure 10:
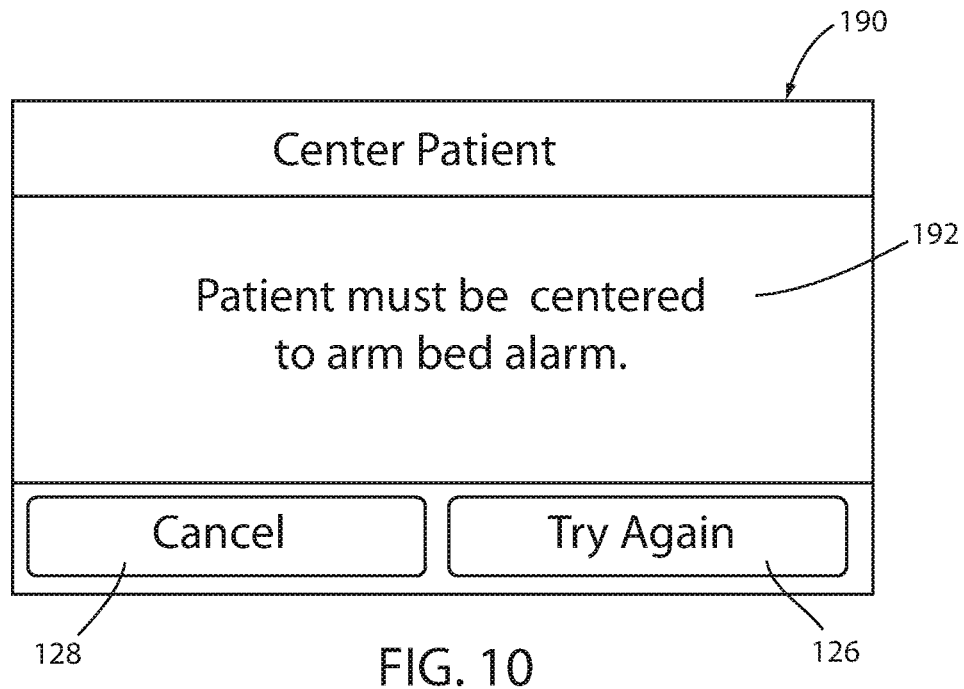
FIG. 10 is a patient centering error screen displayable on the control panel of FIG. 4.

Returning to step 150 of algorithm 140 (FIG. 7), if exit detection system 52 is not able to complete all of the prerequisite transition tasks and arm itself (or change sensitivity levels), it moves to step 154 where, in some embodiments, it displays a message to the user notifying him or her of the unsuccessful arming process. FIG. 10 shows one example of such a message that is displayed at step 154. This specific message is displayed when the transition task of confirming that the patient's center of gravity 116 remains within the desired active zone for the minimum amount of time is unable to be completed. Other types of messages may be displayed, and the content of the message may vary depending upon which transition task was unable to be completed.

For at least one of the transition tasks that could not be completed, exit detection system 52 is configured to invite the user to either retry the arming process or to cancel the arming process. This invitation is completed at step 154 (FIG. 7) and comprises displaying a retry option icon 126 and a cancel option icon 128, examples of which are shown in FIG. 10. At step 166, controller 72 determines if the user has selected the cancel option icon 126. If so, controller 72 proceeds to step 168. If not, controller 72 proceeds to step 178.

At step 168 (FIG. 7), controller 72 determines if exit detection system 52 was previously armed or not. That is, controller 72 determines if the user activated the arming control at step 144 in order to change a currently armed exit detection system 52 from a first sensitivity level to a different sensitivity level, or in order to change a currently unarmed exit detection system 52 to an armed state. In the former case, controller 72 proceeds to step 172. In the latter case, it proceeds to step 174. In either case, controller 72 automatically exits the transition mode.

At step 172, controller 72, after having automatically exited from the transition mode 134 at step 168, determines which mode 130a-c it was operating in immediately prior to the user activating a control at step 144. After making this determination, controller 72 automatically returns to this user-selected mode and proceeds to operate in this mode at step 152.

At step 174, controller 72, after having automatically exited from the transition mode 134 at step 168, displays a message on display 80 of control panel 54, that it was either unable to arm exit detection system 52 or that the arming process has been canceled. Controller 72 then places exit detection system 52 in a disarmed state and returns to step 142.

Returning to step 166 (FIG. 7), if the user does not select the cancel option (e.g. cancel option icon 128), controller 72 proceeds to step 178 where it determines if the user has selected the retry option (e.g. by pressing on retry option icon 126). If the user has selected the retry option, controller 72 returns to step 148 where it makes another attempt to complete the one or more transition tasks necessary to arm exit detection system 52. If the user does not select the retry option at step 178, controller 72 proceeds to step 176, where it determines if a transition timer has expired. The transition timer is started when the user is first presented with the cancel or retry option at step 154. If the transition timer has not yet expired at step 176, controller 72 returns to step 154 where it continues to invite the user to cancel or retry the arming of exit detection system 52. If the transition timer has expired at step 176, controller 72 proceeds to step 168 and automatically exits from transition mode 134. At step 168, controller 72 proceeds in the manner previously described.

The transition timer that is initiated the first time that step 154 is executed may vary in length. In some embodiments, it is on the order of twenty to forty seconds. The transition timer corresponds to how long control panel 54 will continue to display a message inviting the user to cancel or retry the arming process before proceeding to self-terminate the arming process. In other words, if control panel 54 invites the user to either cancel or retry the arming process, but the user declines to make either choice, controller 72 will self-terminate the arming process after the transition timer has expired. The length of time of this timer should therefore be long enough to give the user sufficient time to make either choice, but not so long as to keep the exit detection system 52 in the transition mode for an excessive amount of time. As noted, the precise value of this length of time may vary.

During the operation of automatic mode selection algorithm 140, controller 72 may be configured to display a number of different messages and/or screens on display 80 of control panel 54. For example, when controller 72 commences operation in the transition mode, such as at steps 146 and/or 148, controller 72 may display a screen notifying the user that the arming process is in progress. One example of such an arming screen 170 is shown in FIG. 8. As can be seen therein, arming screen 170 includes an arming icon 182 that, in some embodiments, moves (e.g. spins in a circular motion) while the arming process is in progress.

Figure 9:
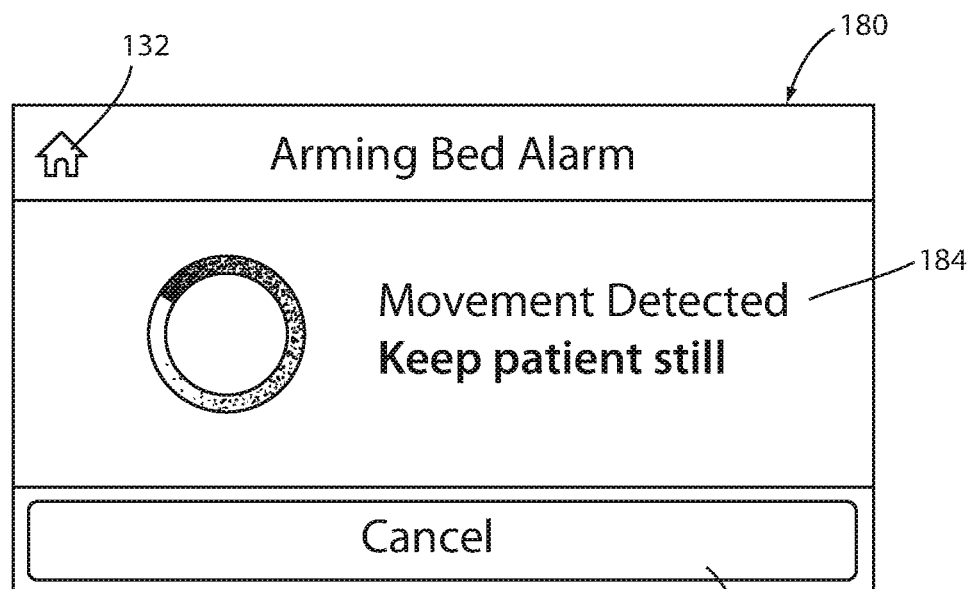
FIG. 9 is a movement caution screen displayable on the control panel of FIG. 4.

In some embodiments, controller 72 is also configured to display one or more reminder messages to the user instructing the user to take one or more actions during the arming process. One example of this is the movement caution screen 180 shown in FIG. 9. Movement caution screen 180 includes a message 184 to the user indicating that movement of the patient has been detected and that the patient should be kept still during the arming process of exit detection system 52. Other types of messages can, of course, be displayed, depending upon what transition tasks are being carried out and/or depending upon what transition task cannot be completed. Such other messages may, for example, instruct the user to set the brake, to plug patient support apparatus 20 into an AC wall outlet, to move the patient to a different location on support deck 30, etc.

Another message that may be displayed by exit detection system 52 on display 80 of control panel 54 during the arming of exit detection system 52 is an error message, such as the patient centering error screen 190 of FIG. 10. Patient centering error screen 190 includes a message 192 indicating that the patient was not properly centered during the arming process (e.g. did not have his or her center of gravity 116 positioned inside of the desired zones 120 for the minimum amount of time). Patient centering error screen 190 also includes the retry option icon 126 and the cancel option icon 128 that allow the user to either retry the arming process or cancel the arming process, as discussed previously.

Although not illustrated in FIG. 7, algorithm 140 is configured to allow the user to cancel the arming process at times other than at step 166. For example, algorithm 140 may be modified to allow the user to cancel the arming process at any time from step 146 to step 154, or at other times. In some embodiments, this cancellation may be accomplished by pressing on a home screen icon 132 that is present on a number of different screen shown on display 80 (e.g. screens 100, 170, and 180 of FIGS. 4, 8, and 9, respectively). This cancellation may also be accomplished by the user pressing on the cancel option icon 128 that is displayed on some of the other screens shown on display 80 (e.g. screens 170, 180, and 190 of FIGS. 8, 9, and 10, respectively). Regardless of which ones of these cancellation options the user activates, algorithm 140 is configured to proceed to step 168 after one of these cancellation options is selected, where it exits the transition mode 134 and either returns to operating in the previously activated user selected mode 130 or returns to the disarmed state.

Figure 11:
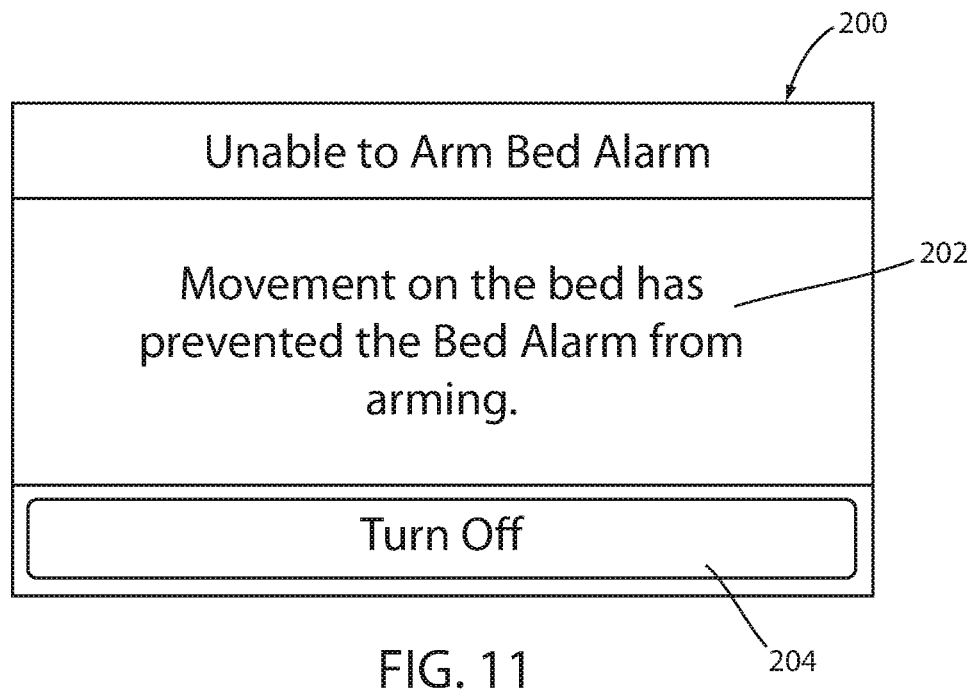
FIG. 11 is an unable-to-arm message screen displayable on the control panel of FIG. 4.

It will be understood that algorithm 140 can be modified in a number of different respects. As but one example, if exit detection system 52 is unable to arm itself, instead of presenting the user with both a retry and a cancel option (e.g. step 154), exit detection system 52 may be configured to present the user with only a cancel option. When modified in this manner, controller 72 may be configured to display a message on display 80 of the type shown in the unable-to-arm screen 200 of FIG. 11. Unable to arm screen 200 includes a message 202 indicating to the user that exit detection system 52 was unable to arm itself during the transition mode because the patient was moving too much for it to complete the transition task of achieving a steady weight reading for the minimum amount of time. This message includes a "turn off" option icon 204. When the user selects this turn off option, exit detection system 52 may be configured to automatically switch out of its current transition mode and execute step 168, or it may be configured to automatically switch out of the current transition mode and move to a disarmed state (regardless of whether it was previously armed or not). In either situation, the user is free to re-attempt arming of the exit detection system by once again manipulating one or more controls on control panel 54.

Figure 12:
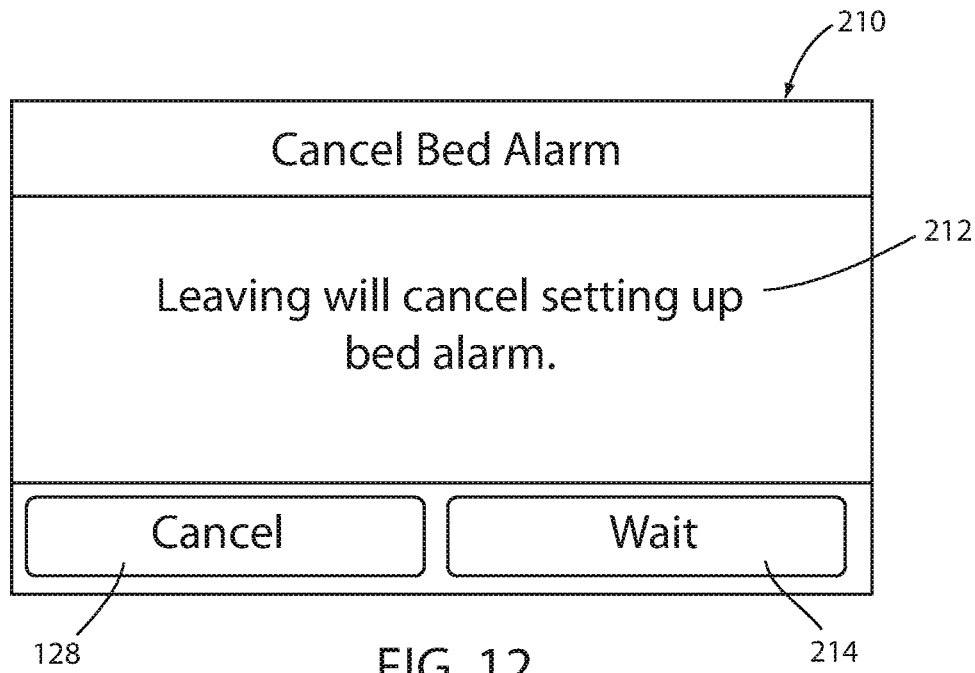
FIG. 12 is an exit detection confirmation screen for confirming the user wishes to cancel the arming process that is displayable on the control panel of FIG. 4.

In some embodiments, exit detection system 52 is also configured to display a cancellation confirmation screen when the user takes an action to cancel the arming of exit detection system 52. Such a confirmation screen forces the user to confirm his or her intentions of cancelling the arming process. One example of such a screen is shown in FIG. 12. FIG. 12 illustrates a cancellation confirmation screen 210 that controller 72 is configured to display on display 80 when the user takes an action for cancelling the arming process. For example, a user may press home screen icon 132 at any point during the arming process of exit detection system 52, and this pressing causes controller 72 to display a screen such as cancellation confirmation screen 210. In this embodiment, a user is only able to navigate to a different screen on display 80 during the arming process if the user cancels the arming process. Thus, screen 210 includes the warning message 212 that leaving the previously displayed screen will cause exit detection system 52 to cancel its arming process, and it presents the user with the option of either waiting for the arming process to finish or cancelling the arming process. The user selects the former by pressing the wait icon 214 and selects the latter by pressing the cancel icon 128.

Another modification that may be made to algorithm 140 is the switching of exit detection system 52 directly from a motion mode to a transition mode. In such modified embodiments, controller 72 may be configured to monitor controls (such as control 78a) while operating in motion mode 136 and, if the control 78a is activated while motion is taking place, to switch to operating in transition mode 134. Similarly, algorithm 140 may be modified to allow exit detection system 52 to switch directly from a transition mode 134 to a motion mode 136 while the exit detection system is in the transition mode 134. Still other modifications are possible.

It will also be understood that, in some embodiments, exit detection system 52 is configured to also make adjustments to the size, shape, and/or position of alert zones 120a-c based on component movement independent of any of motion modes 136a-c. Such additional adjustments, in some embodiments, are made by exit detection system 52 in response to the movement of components for which no real time position feedback is available, as discussed above. Thus, for example, if a siderail is moved from a raised position to a lowered position, exit detection system 52 is configured to make an adjustment to the currently active zone 120a-c at the time that the new position of the siderail is detected, regardless of whether the siderail movement occurs, either or wholly or partially, during operation of any of user-selectable modes 130a-c, transition modes 134a-b, and/or motion modes 136a-c. In still other embodiments, these adjustment may be postponed until exit detection system 52 returns to one of its user-selectable modes 130a-c.

Figure 13:
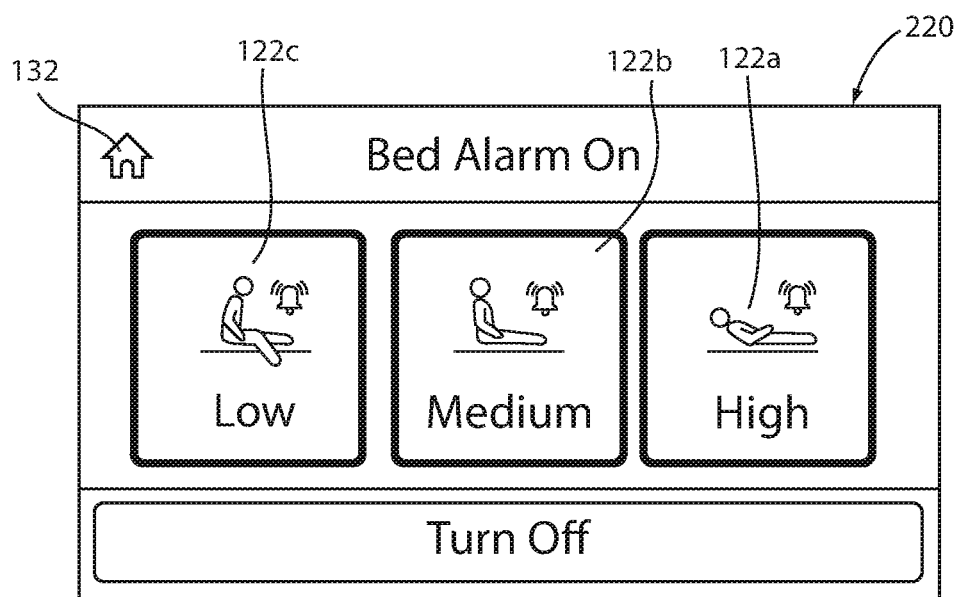
FIG. 13 is another exit detection arming screen displayable on the control panel of FIG. 4.

After a user has successfully armed exit detection system 52, or switched its operation from a first sensitivity level to a second sensitivity level, controller 72 is configured, in at least one embodiment, to display another arming screen, such as arming screen 220 of FIG. 13. Arming screen 220 is the same as arming screen 100 of FIG. 4 except that controller 72 has highlighted the highest sensitivity icon 122a instead of the medium sensitivity icon 122b, as in FIG. 4. Thus, controller 72 may be configured to display arming screen 220 after the user has armed exit detection system 52 with its highest sensitivity level. Similarly, although not shown, if exit detection system 52 is armed with its lowest sensitivity level, controller 72 may be configured to highlight lowest sensitivity icon 122c.

It will also be understood that, although exit detection system 52 has been described herein as primarily being controlled via control panel 54, patient support apparatus 20 may be configured to allow exit detection system 52 to be controlled via one or more portable electronic devices 92. Such devices may be configured to display the same, or similar, screens on display 94 as those shown and described herein as being displayed on screen 80, thereby presenting the user of the portable device 92 with the same options and screens that he or she generally sees on display 80 of control panel 54. In this manner, there is little visual difference to the user between controlling exit detection system 52 via control panel 54 and via a mobile electronic device 92. As was noted previously, such mobile electronic devices 92 may be further configured to control other aspects of patient support apparatus 20, and/or to carry out other functions for assisting the caregiver.

Although exit detection system 52 has been primarily described herein as computing a center of gravity 116 of the occupant and comparing the position of the computed center of gravity to an active zone 120, it will be understood by those skilled in the art that exit detection system 52 can be modified to process the outputs of force sensors 74 in other manners besides computing a center of gravity 116. For example, controller 72 may be configured to sum the total amount of force on force sensors 74 when patient support apparatus 20 is occupied and then looks for shifts of more than a threshold amount of that weight to a side, head end, or foot end of patient support apparatus. For example, if a 100 kilogram person is occupying patient support apparatus 20, exit detection system 52 may be modified to trigger an exit alert if more than X percent, say, 70% (0.70×100=70 kilograms) of the total forces are detected by the two force sensors 74 positioned along the right side of patient support apparatus 20, or by the two force sensors 74 positioned along the left side of patient support apparatus 20. In some embodiments, a different ratio of the forces detected by the two force sensors 74 positioned along the foot end 40 of patient support apparatus 20 may trigger an exit alert if the ratio exceeds a different threshold, while still another ratio of the forces detected by the two force sensors 74 positioned along the head end 38 of patient support apparatus 20 may trigger an exit alert if that ratio exceeds yet a different threshold. In sum, exit detection system 52 can be modified to compute one or more ratios of the force detected by a first force sensor 74 (or the sum of forces detected by a combination of first force sensors 74) to the force, or sum of forces, detected by at least one other force sensor 74. The one or more ratios may then be compared to one or more thresholds for determining whether to issue an exit alert or not. Other types of weight distribution changes may also be used to trigger an exit alert.

When exit detection system 52 is implemented to compute one or more force ratios based on the outputs of force sensors 74 instead of a center of gravity of the occupant, controller 72 modifies the threshold(s) used by exit detection system 52 either during, or after exiting, its motion mode 136. In such embodiments, the references to adjusting a zone boundary in FIG. 6 are implemented as changes in the thresholds to which the ratio(s) are compared, rather than changes in the boundary of an area defined in frame of reference 108.

Exit detection system 52 may also be modified to use and analyze the outputs of non-force sensors, either in addition to or in lieu of the outputs from force sensors 74. For example, the principles disclosed herein can be applied to a video image based exit detection system wherein an exit alert is issued if the position of the occupant meets one or more criteria (e.g. the occupant moves to within X distance of a side of patient support apparatus 20). Based on one or more of the factors discussed herein (e.g. width of the support deck 30, incline angle of the litter frame 28, lateral rotation therapy status, addition or removal of a non-occupant object, etc.), the exit detection system may alter one or more of the criteria (e.g. distance X) based upon these factors. Still other types of exit detection systems may be used in accordance with these principles, including, but not limited to, thermal imaging based exit detection systems, accelerometer based exit detection systems, radar based exit detection systems, pressure sensing exit detection systems, and others.

As was previously noted, controller 72 of exit detection system 52 may be further configured to change the boundary of the zone(s) 120 during any of modes 130*a-c* in response to a variety of different triggers. These triggers includes, but are not limited to, movement of components for which real time position feedback is not available (e.g. the raised/lowered position of siderail 36, a width of deck 30, a length of deck 30, etc.), a patient characteristic, the addition or removal of an object from litter frame 28, the implementation of a mattress therapy (e.g. lateral rotation), or still other factors. Several manners in which the zones 120*a-c* may be adjusted in response to a patient characteristic are disclosed in the commonly assigned U.S. patent application Ser. No. 15/266,575, which has already been incorporated herein by reference. Further, methods for automatically identifying the addition or removal of a non-patient object on a patient support apparatus using force sensors 74 are disclosed in commonly assigned U.S. Patent Application Publication No. 2016/0022218 to Hayes et al., entitled PATIENT SUPPORT APPARATUS WITH PATIENT INFORMATION SENSORS, the complete disclosure of which is hereby incorporated herein by reference. In general, any one of the triggers for adjusting a boundary of an alert zone disclosed in commonly assigned 62/889,254 application (incorporated by reference previously herein) may be used by exit detection system 52 to adjust one or more of the boundaries of zones 120*a-c*, either while in a user-selectable mode 130*a-c*, or while in one of the motion or transition modes 134 and/or 136.

It will also be understood that all of the aforementioned adjustments to alert zones 120*a-c* and/or to the patient's calculated center of gravity are accomplished based on readings taken from force sensors 74 that are, in at least one embodiment, automatically adjusted in order to compensate for errors introduced into these sensor readings from litter frame 28 being non-level. That is, in some embodiments, force sensors 74 are load sensors whose outputs do not reflect the true load placed thereon when the load applied to the load cell is tilted, such as may happen when litter frame 28 is tilted out of a horizontal orientation. In such cases, the level of tilt is detected by one or more sensors onboard patient support apparatus 20 and a simple trigonometric calculation (based on the detected tilt angle) is applied to the outputs of the load cells 74 to remove this error in the load measurement. These tilt-adjusted load cell readings are then processed and used to compute the center of the gravity of the patient and/or the distribution of the patient's weight, along with the concomitant changes, as appropriate, to the alert zones 120*a-c* discussed above.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a frame;
a support surface supported by the frame and adapted to support a patient thereon;
an exit detection system adapted to be armed and disarmed, the exit detection system further adapted to operate, when armed, in a first mode with a first sensitivity level or in a second mode with a second sensitivity level, wherein the exit detection system is adapted to issue an alert if movement of the patient beyond a first threshold occurs while operating in the first mode and to issue the alert if movement of the patient beyond a second threshold occurs while operating in the second mode;

a control panel in communication with the exit detection system and adapted to allow a user to arm and disarm the exit detection system and to change the exit detection system from the first mode to the second mode, wherein the exit detection system is further adapted to, in response to the user activating a control to change from the first mode to the second mode, to operate in a transition mode during a transition period defined between a first moment when the user activates the control and a second moment when the exit detection system actually begins operating in the second mode or returns to operating in the first mode, wherein while the exit detection system is operating in the transition mode, the exit detection system is adapted to issue the alert if movement of the patient beyond a transition threshold occurs; and a motion sensor in communication with the exit detection system, wherein the motion sensor is adapted to detect movement of a component of the patient support apparatus, and wherein the exit detection system is further adapted to perform the following: (a) override the exit detection system's current mode of operation with a motion mode of operation when the component is moved, and to cease operating in the motion mode after the component has been moved; (b) not issue the alert when operating in the motion mode if movement of the patient beyond any of the first threshold, second threshold, or transition thresholds occurs; and (c) issue the alert in the motion mode only if the weight of the patient decreases by ten percent or more.

2. The patient support apparatus of claim 1 further comprising a second motion sensor adapted to detect movement of a second component of the patient support apparatus, wherein the exit detection system is further adapted to override the exit detection system's current mode of operation with the motion mode of operation when at least one of the component or the second component is moved, and to cease operating in the motion mode after the at least one of the component or the second component has been moved.

3. The patient support apparatus of claim 2 wherein the first, second, and transition thresholds correspond to first, second, and transition zones, respectively, that each define permitted areas of movement of a center of gravity of the patient, and wherein the exit detection system is adapted to recalculate a boundary of the first, second, and/or transition zone while operating in the motion mode, and the recalculation varies based upon whether the component or the second component has been moved.

4. The patient support apparatus of claim 1 wherein the exit detection system is further adapted to:
(a) operate in a third mode with a third sensitivity level different from the first and second sensitivity levels, wherein the transition threshold corresponds to whichever one of the first, second, and third sensitivity levels has the least sensitivity;
(b) perform a transition task during the transition period, wherein the transition task is a prerequisite for changing from the first mode to the second mode, and the control panel includes a display adapted to display a message during the transition period if the exit detection system is unable to complete the transition task;
(c) present the user with a retry choice or a cancel choice if the exit detection system is unable to complete the transition task, wherein the retry choice comprises re-attempting to change from the first mode to the second mode and the cancel choice comprises canceling the change of the exit detection system from the first mode to the second mode; and
(d) await a predetermined time period after presenting the user with the retry and cancel choices and, if the user does not make a choice, to automatically stop operating in the transition mode and to return to operating in the first mode.

5. The patient support apparatus of claim 4 wherein the exit detection system includes a plurality of force sensors and the transition task includes at least one of the following: (a) taking stable readings from the plurality of force sensors for a predetermined period of time; (b) confirming that a brake on the patient support apparatus is engaged; or (c) confirming that the patient support apparatus is not operating on power from a battery having a charge level below a predetermined charge threshold.

6. The patient support apparatus of claim 4 wherein the exit detection system is further adapted to continue to operate in the transition mode until either the exit detection system changes to operating in the second mode or the user discontinues attempts to change the exit detection system to operating in the second mode.

7. The patient support apparatus of claim 1 further comprising a motion controller adapted to control movement of a second component of the patient support apparatus, wherein the exit detection system is further adapted to perform the following: (a) override the exit detection system's current mode of operation with the motion mode of operation when the motion controller is moving the second component, and to cease operating in the motion mode when the motion controller stops moving the second component.

8. The patient support apparatus of claim 1 wherein the exit detection system comprises a plurality of load cell adapted to detect forces exerted by the patient on the support surface and a controller in communication with the plurality of load cells.

9. The patient support apparatus of claim 1 wherein the component is at least one of the following: a siderail, a portion of the support surface adapted to allow a length of the support surface to be changed, or a portion of the support surface adapted to allow a width of the support surface to be changed.

10. The patient support apparatus of claim 1 wherein the exit detection system includes a plurality of force sensors adapted to detect a weight of the patient and the exit detection system is adapted to, after the component has been moved, to automatically begin operating in whichever mode the exit detection system was operating in prior to commencement of the motion mode.

11. The patient support apparatus of claim 1 wherein the transition threshold corresponds to whichever of the first and second sensitivity levels is smaller.

12. The patient support apparatus of claim 1 wherein the transition threshold corresponds to a threshold less restrictive than at least one of the first sensitivity level or the second sensitivity level.

13. A patient support apparatus comprising:
a frame;
a support surface supported by the frame and adapted to support a patient thereon;
an exit detection system adapted to be armed and disarmed, the exit detection system further adapted to operate, when armed, in a first mode with a first sensitivity level or in a second mode with a second sensitivity level, wherein the exit detection system is adapted to issue an alert if movement of the patient beyond a first threshold occurs while operating in the first mode and to issue the alert if movement of the patient beyond a second threshold occurs while operating in the second mode;
a motion sensor in communication with the exit detection system, the motion sensor adapted to detect movement of a component of the patient support apparatus; and
a control panel in communication with the exit detection system and adapted to allow a user to arm and disarm the exit detection system and to change the exit detection system from the first mode to the second mode and vice versa, wherein the exit detection system is further adapted to override the exit detection system's current mode of operation with a motion mode of operation when the component is moved, and to cease operating in the motion mode after the component has been moved, wherein the exit detection system generates the alert while in the motion mode of operation in a manner different from how the exit detection system generates the alert while in either the first mode or second mode of operation.

14. The patient support apparatus of claim 13 wherein the exit detection system further includes a plurality of load cells adapted to detect a weight of the patient, and the exit detection system is further adapted to not issue the alert when operating in the motion mode if movement of the patient beyond either of the first threshold or the second threshold occurs, but to issue the alert in the motion mode if the weight of the patient decreases by ten percent or more.

15. The patient support apparatus of claim 13 further comprising a second motion sensor adapted to detect movement of a second component of the patient support apparatus, wherein the exit detection system is further adapted to override the exit detection system's current mode of operation with the motion mode of operation when at least one of the component or the second component is moved, and to cease operating in the motion mode after the at least one of the component or the second component has been moved.

16. The patient support apparatus of claim 15 wherein the exit detection system is adapted to calculate a center of gravity of the patient while operating in either of the first or second modes, and to stop calculating the center of gravity of the patient while operating in the motion mode, and wherein the first and second thresholds correspond to first and second zones, respectively, that each define permitted areas of movement of the center of gravity of the patient, and wherein the exit detection system is adapted to recalculate a boundary of the first or second zone while operating in the motion mode, and the recalculation varies based upon whether the component or the second component has been moved.

17. The patient support apparatus of claim 13 wherein the exit detection system is further adapted to perform the following, in response to the user activating a control to change from the first mode to the second mode:
to attempt to complete a transition task wherein the transition task is a prerequisite to changing from the first mode to the second mode;
to notify the user if the exit detection system is unable to complete the transition task;
to present the user with a retry choice and a cancel choice, wherein the retry choice comprises re-attempting to change from the first mode to the second mode and the cancel choice comprises canceling changing from the first mode to the second mode;
to await a predetermined time period after presenting the user with the retry and cancel choices; and
to automatically return to operating in the first mode if the user does not select the retry choice or the cancel choice within the predetermined time period.

18. The patient support apparatus of claim 13 further comprising a control panel in communication with the exit detection system and adapted to allow a user to arm and disarm the exit detection system and to change the exit detection system from the first mode to the second mode, wherein the exit detection system is further adapted to, in response to the user activating a control to change from the first mode to the second mode, to operate in a transition mode during a transition period defined between a first moment when the user activates the control and a second moment when the exit detection system actually begins operating in the second mode or returns to operating in the first mode, wherein while the exit detection system is operating in the transition mode, the exit detection system is adapted to issue the alert if movement of the patient beyond a transition threshold occurs, wherein the transition threshold corresponds to whichever of the first and second sensitivity levels is smaller.

19. The patient support apparatus of claim 13 further comprising a control panel in communication with the exit detection system and adapted to allow a user to arm and disarm the exit detection system and to change the exit detection system from the first mode to the second mode, wherein the exit detection system is further adapted to, in response to the user activating a control to change from the first mode to the second mode, to operate in a transition mode during a transition period defined between a first moment when the user activates the control and a second moment when the exit detection system actually begins operating in the second mode or returns to operating in the first mode, wherein while the exit detection system is operating in the transition mode, the exit detection system is adapted to issue the alert if movement of the patient beyond a transition threshold occurs, wherein the transition threshold corresponds to a threshold less restrictive than at least one of the first sensitivity level or the second sensitivity level.

20. The patient support apparatus of claim 13 wherein the component is at least one of the following: a siderail, a portion of the support surface adapted to allow a length of the support surface to be changed, or a portion of the support surface adapted to allow a width of the support surface to be changed.

* * * * *